United States Patent [19]
Phipps

[11] Patent Number: 5,533,971
[45] Date of Patent: Jul. 9, 1996

[54] REDUCTION OF SKIN IRRITATION DURING ELECTROTRANSPORT

[75] Inventor: Joseph B. Phipps, Plymouth, Minn.

[73] Assignee: Alza Corporation, Palo Alto, Calif.

[21] Appl. No.: 116,660

[22] Filed: Sep. 3, 1993

[51] Int. Cl.⁶ ..................................... A61N 1/30
[52] U.S. Cl. ................ 604/20; 604/890.1; 604/290; 607/115
[58] Field of Search ................ 604/20, 65–66, 604/290, 890.1; 607/149–152, 115; 436/74, 79, 55; 128/637

[56] References Cited

U.S. PATENT DOCUMENTS

| | | | |
|---|---|---|---|
| 3,989,050 | 11/1976 | Buchalter | 128/419 |
| 3,991,755 | 11/1976 | Vernon et al. | 128/172.1 |
| 4,163,039 | 7/1979 | Emrich . | |
| 4,164,226 | 8/1979 | Tapper | 128/419 |
| 4,211,222 | 7/1980 | Tapper | 128/207.21 |
| 4,299,231 | 11/1981 | Karmann et al. | 128/639 |
| 4,301,794 | 11/1981 | Tapper | 128/207.21 |
| 4,340,047 | 7/1982 | Tapper et al. | 128/207.21 |
| 4,416,274 | 11/1983 | Jacobsen et al. | 604/20 |
| 4,444,193 | 4/1984 | Fogt et al. . | |
| 4,474,570 | 10/1984 | Ariura et al. | 604/20 |
| 4,702,732 | 10/1987 | Powers et al. | 604/20 |
| 4,708,716 | 11/1987 | Sibalis | 604/20 |
| 4,717,378 | 1/1988 | Perrault et al. | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,752,372 | 6/1988 | Rhodes et al. | 204/299 |
| 4,764,164 | 8/1988 | Sasaki | 604/20 |
| 4,786,277 | 11/1988 | Powers et al. | 604/20 |
| 4,810,418 | 3/1989 | Burvee | 252/500 |
| 4,842,701 | 6/1989 | Smith et al. | 204/180.1 |
| 4,846,182 | 7/1989 | Fogt et al. . | |
| 4,872,956 | 10/1989 | Kotani . | |
| 4,886,489 | 12/1989 | Jacobsen et al. | 604/20 |
| 4,915,685 | 4/1990 | Petelenz et al. | 604/20 |
| 4,973,303 | 11/1990 | Johnson et al. | 604/20 |
| 5,042,975 | 8/1991 | Chien et al. | 604/20 |
| 5,088,978 | 2/1992 | Hillman et al. | 604/20 |
| 5,116,759 | 5/1992 | Klainer et al. . | |
| 5,120,545 | 6/1992 | Ledger et al. | 424/449 |
| 5,125,894 | 6/1992 | Phipps et al. | 604/20 |
| 5,135,477 | 8/1992 | Untereker et al. | 604/20 |
| 5,203,327 | 4/1993 | Schoendorfer et al. . | |
| 5,362,307 | 11/1994 | Guy et al. . | |

FOREIGN PATENT DOCUMENTS

| | | |
|---|---|---|
| 631424 | 11/1963 | Canada . |
| 0278473 | 8/1988 | European Pat. Off. ....... A61K 37/02 |
| 0299631 | 1/1989 | European Pat. Off. . |
| WO8607269 | 12/1986 | WIPO . |
| WO9111215 | 8/1991 | WIPO ............... A61B 1/30 |
| WO9303790 | 3/1993 | WIPO ............... A61N 1/30 |

OTHER PUBLICATIONS

Ledger, Philip W., "Skin biological issues in electrically enhanced transdermal delivery", Advanced Drug Delivery Reviews, 9 (1992) pp. 289–307.

(List continued on next page.)

Primary Examiner—Randall L. Green
Assistant Examiner—Mark Bockelman
Attorney, Agent, or Firm—D. Byron Miller; Steven F. Stone; Edward L. Mandell

[57] ABSTRACT

An electrotransport delivery device utilizing reservoir buffering at a select pH ranges in order to reduce skin irritation and skin resistance is provided. Cathodic reservoirs are buffered to a pH of less than about 4, preferably to a pH in the range of about 2 to 4, while anodic reservoirs are buffered to a pH above about 4, preferably to a pH in the range of about 4 to 10. Another electrotransport delivery device utilizes a potassium sensor to monitor potassium efflux from the skin. Potassium efflux above a certain predetermined level has been found to be a precursor to skin irritation/erythema. Operation of the device is modified (eg, terminated) when the predetermined potassium efflux level is sensed.

15 Claims, 9 Drawing Sheets

OTHER PUBLICATIONS

Schwarz, V., et al., "Some Hazards of the Sweat Test", Arch. Dis. Childh., 1968, vol. 43, pp. 695–701.

Yoshida, Nagahiro H., et al., "Structure–transport relationships in transdermal iontophoresis", Advanced Drug Delivery Reviews, vol. 9 (1992) pp. 239–264.

Burnette, Ronald R., et al., "Comparison Between the Iontophoretic and Passive Transport of Thyrotropin Releasing Hormone Across Excised Nude Mouse Skin", Journal of Pharmaceutical Sciences, vol. 75, No. 8, Aug. 1986, pp. 738–743.

Allenby, A. C., et al., "The Effect of Heat, pH and Organic Solvents on the Electrical Impedance and Permeability of Excised Human Skin", Br. J. Dermatol., 1969, 81, Suppl. 4, pp. 31–39.

Sanderson, John E., et al., "Inotophoretic Delivery of Nonpeptide Drugs: Formulation Optimization for Maximum Skin Permeability", Journal of Pharmaceutical Sciences, vol. 78, No. 5, May 1989, pp. 361–364.

Molitor, H., et al., "Studies on Iontophoresis: Experimental Studies on the Causes and Prevention of Iontophoretic Burns", American Journal of Medical Science, No. 198 (1939).

Siddiqui, Ovais, et al., "Facilitated Transdermal Transport of Insulin", Journal of Pharmaceutical Sciences, vol. 76, No. 4, Apr. 1987, pp. 341–345.

Morimoto, Kazuhiro, et al., "Effects of Proteolytic Enzyme Inhibitors as Absorption Enhancers on the Transdermal Iontophoretic Delivery of Calcitonin in Rats", J. Pharm. Pharmacol., 1992, vol. 44, pp. 216–218.

Morimoto, Kazuhiro, et al., "Effects of proteolytic enzyme inhibitors of enhancement of transdermal iontophoretic delivery of vasopressin and an analogue in rats", International Journal of Pharmaceutics, vol. 81, (1992) pp. 119–125.

Nightingale, J., et al., "Effect of pH on the Iontophoretic Delivery of Ionic Compounds", Proceed. Intern. Symp. Control. Rel. Bioact. Mater., 17 (1990), Controlled Release Society, Inc.

Chien, Yie W., "Transdermal Route of Peptide and Protein Drug Delivery", Rutgers, State University of New Jersey, Piscataway, New Jersey, Marcel Dekker, Inc., pp. 667–689.

Kumar, Saran, et al., "In Vivo Transdermal Iontophoretic Delivery of GRF (1–44) in Hairless Guinea Pigs", Proceed. Intern. Symp. Control. Rel. Bioact. Mater., 17 (1990), Controlled Release Society, Inc., pp. 435–436.

Siddiqui, Ovais, et al., "The effect of iontophoresis and vehicle pH on the in-vitro permeation of lignocaine through human stratum corneum", J. Pharm. Pharmacol., 1985, vol. 37, pp. 732–735.

Wearley, Lorraine, et al., "Iontophoresis–facilitated transdermal delivery of verapamil. 1. In Vitro Evaluation and Mechanistic Studies", Journal of Controlled Release, vol. 8, (1989) pp. 237–250.

Wearley, Lorraine, et al., "Iontophoresis–facilitated transdermal delivery of verapamil. II. Factors Affecting the Reversibility of Skin Permeability", Journal of Controlled Release, vol. 9, (1989) pp. 231–242.

Preat, V., et al., "Iontophorectic Transport of Fentanyl and Syufentanyl", Proceed. Intern. Symp. Cotnrol. Rel. Bioact. Mater., vol. 18, (1991), Controlled Release Society, Inc., pp. 605 . 606.

Sarpotdar, Pramod P., "Iontophoresis", Cosmetics & Toiletries, vol. 106, Jun. 1991, pp. 94–100.

Chien, Yie W., et al., "Direct Current Iontophoretic Transdermal Delivery of Peptide and Protein Drugs", Journal of Pharmaceutical Sciences, vol. 78, No. 5, May 1989, pp. 376–383.

Siddiqui, Ovais, et al., "Iontophoretic transport of weak electrolytes through the excised human stratum corneum", J. Pharm. Pharmacol., 1989, vol. 41, pp. 430–432.

Miller, Larry, L., et al., "Iontophoretic transport of acetate and carboxylate ions through hairless mouse skin. A cation exchange membrane model", International Journal of Pharmaceutics, vol. 49, (1989), pp. 15–22.

Sims, S. M., et al., "Baseline Studies on Iontophoretic Transport in Hairless Mouse Skin: The Effect of Applied Voltage Drop and pH on the Iontophoresis of a Model Weak Electrolyte", Journal of Membrane Science, vol. 49, (1990) pp. 305–320.

Cullander, Christopher, et al., "Sites of Iontophoretic Current Flow into the Skin: Identificatiofn and Characterization with the Vibrating Probe Electrode", The Society for Investigative Dermatology, Inc., (1991), vol. 97, No. 1.

Benjamin, F. B., et al., "Sodium–Potassium Ratio of Human Skin as Obtained by Reverse Iontophoresis", Journal of Applied Physiology, vol. 6, Jan. 1954, pp. 401–407.

Singh, J., "Effect of pH on iontophoretic and passive transport of p–amino benzoic acid through full thickness rat skin", Pharmazie, vol. 45 (1990), H. 8, p. 634.

Ghanem, Abdel–Halim, et al., "A Quantitative Approach for Studying the Influence of pH on Transdermal Formulations of Weak Electrolyte Drugs", Proceed. Intern. Symp. Control. Rel. Bioact. Mater., vol. 17 (1990), Controlled Release Society, Inc., pp. 305–306.

Chien, Y. W., et al., "Iontophoresis–facilitated Transdermal Delivery of Peptide and Protein", Journal of Controlled Release, vol. 13, pp. 263–278.

REDUCTION OF SKIN IRRITATION DURING ELECTROTRANSPORT

TECHNICAL FIELD

This invention relates to electrotransport agent delivery devices, compositions, and methods. More particularly, this invention relates to methods of reducing skin irritation and electrical skin resistance during transdermal electrotransport agent delivery.

BACKGROUND ART

The term "electrotransport" as used herein refers generally to the delivery of an agent (eg, a drug) through a membrane, such as skin, mucous membrane, or nails, which delivery is induced by application of an electrical potential. For example, a beneficial therapeutic agent may be introduced into the systemic circulation of a human body by electrotransport delivery through the skin. A widely used electrotransport process, iontophoresis, involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field, through which pores an agent can be delivered either passively (ie, without electrical assistance) or actively (ie, under the influence of an electric potential). However, in any given electrotransport process, more than one of these processes may be occurring simultaneously to a certain extent.

Accordingly, "electrotransport", as used herein, should be given its broadest possible interpretation so that it includes the electrically induced or enhanced transport of at least one agent, which may be charged, uncharged, or a mixture thereof, regardless of the specific mechanism or mechanisms by which the agent actually is transported.

Electrotransport devices generally use at least two electrodes which are in electrical contact with some portion of the skin, nails, mucous membrane, or other surface of the body. One electrode, commonly referred to as the "donor" or "active" electrode, is the electrode from which the agent is delivered into the body. The other electrode, typically termed the "counter" or "return" electrode, serves to close the electrical circuit through the body. For example, if the agent to be delivered is positively charged, ie a cation, then the anode will be the active or donor electrode, while the cathode serves to complete the circuit. Alternatively, if an agent is negatively charged, ie an anion, the cathode will be the donor electrode. Additionally, both the anode and cathode may be considered donor electrodes if both anionic and cationic agent ions are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is connected to the donor electrode, while the opposite pole is connected to the counter electrode. In addition, some electrotransport devices have an electrical controller which controls the current applied through the electrodes, thereby regulating the rate of agent delivery. Furthermore, passive flux control membranes, adhesives for maintaining device contact with a body surface, insulating members, and impermeable backing members are some other potential components of electrotransport devices.

Although the advantages of electrotransport delivery are numerous (eg, enhanced transmembrane flux of beneficial agents compared to passive, ie, non-electrically assisted flux; precise control of agent delivery, including patterned delivery, etc.), there are disadvantages under certain application conditions. One potential problem with electrotransport transdermal delivery is skin irritation. For instance, applying electric current through skin under certain conditions has been known to cause skin irritation. See for example, "Skin Biological Issues in Electrically Enhanced Transdermal Delivery", P. Ledger, Advanced Drug Delivery Reviews, Vol. 9 (1992), pp 289–307.

In addition to the level of applied electric current, other factors can cause, or at least contribute to, skin irritation during transdermal electrotransport agent delivery. For example, most electrotransport drug delivery devices use an aqueous solution or suspension of the agent to be delivered, since water is a biocompatible solvent and since many drug salts are water soluble. Under certain conditions, especially in electrotransport devices having electrodes formed of an electrochemically inert (ie, catalytic) material, such as platinum or stainless steel, water hydrolysis tends to occur at the interface between the electrode and the drug solution (donor reservoir) or electrolyte salt solution (counter reservoir). The products of water hydrolysis (ie, hydronium ions are produced by water hydrolysis at the anode and hydroxyl ions are produced by water hydrolysis at the cathode) compete with the drug ions of like charge for delivery into the skin, thereby altering skin pH. Since (i) highly basic or acidic solutions in contact with the skin surface and (ii) highly basic or acidic conditions within the skin itself are known to damage tissue, the pH-altering effects of electrotransport devices, independent of current density effects, can also cause skin irritation.

In order to prevent water hydrolysis, prior art devices used electrodes composed of electrochemically reactive materials (eg, silver anodes and silver chloride cathodes) which materials were oxidized or reduced in lieu of water hydrolysis. See for example Phipps et al U.S. Pat. Nos. 4,744,787 and 4,747,819; Petelenz et al U.S. Pat. No. 4,752,285 and Untereker et al U.S. Pat. No. 5,135,477.

In addition to electrochemically reactive electrode materials, the prior art has also utilized conventional buffering agents to control the pH of the donor and counter reservoirs. See as for example Jacobsen et al U.S. Pat. No. 4,416,274 (sodium phosphate buffers) and Hillman et al U.S. Pat. No. 5,088,978 (citric acid/citrate salt buffers). Although conventional buffers are effective to maintain donor reservoir pH, they introduce undesirable extraneous ions which tend to compete with the drug ions for delivery. For example, when an anodic donor reservoir for delivering a cationic drug $D^+$ is buffered with a citrate salt (eg, sodium citrate), the citrate buffer absorbs hydronium ions produced by water hydrolysis at the anode but leaves extraneous sodium ions which compete with the drug ions, $D^+$, for delivery. Whenever a significant amount of competing ions are present, the rate of drug delivery cannot be accurately predicted simply by measuring or controlling the amount of electric current applied by the device.

In response to these problems, the prior art used buffering agents which were substantially immobile. See Sanderson et al, U.S. Pat. No. 4,722,726 and Johnson et al, U.S. Pat. No. 4,973,303.

Most prior art devices used buffering agents to maintain the donor (drug) and counter (electrolyte) reservoirs at pH levels at or near skin pH. For instance, Hillman et al, U.S. Pat. No. 5,088,978, discloses an anodic electrode buffered at pH 4–5 to resist pH changes associated with proton generation from water hydrolysis. This patent further discloses buffering an "indifferent", cathodic electrode at pH 4–7.

The effects of anodic and cathodic pH on selected buffers in iontophoresis are discussed in "Some Hazards of the Sweat Test" by Schwarz, V. et al, *Arch. Dis. Childh.* (1968) 43,695–701. Carbon and copper electrodes were used in the reported experimentation. This reference indicates that blistering of the skin in contact with either the cathode or anode is dependent upon both the pH and the buffer composition of the anodic and cathodic reservoirs.

However, according to "Structure-Transport Relationships in Transdermal Iontophoresis" by Yoshida et al, *Ad. Drug Del. Rev.* (1992), 9, 239–264, the preferred pH range for avoiding skin irritation for the donor reservoir, independent of the buffer used, is 3 to 8. Outside this pH range, according to this reference, irritation and/or damage of the stratum corneum can occur.

Thus, literature and patent references have presented overlapping pH ranges for minimizing skin irritation. Certain references have focussed primarily on providing neutral solutions or solutions having pH near that of human skin at both the anodic and cathodic reservoirs. Other references are predominantly concerned with counteracting the acidic and caustic irritation problems associated with water hydrolysis at the anode and cathode, respectively. Furthermore, the references have focussed primarily on donor (drug) reservoir pH control since the solubility of the drug in the liquid solvent is in many cases highly dependent on solution pH. Thus, minimizing skin irritation by control of counter reservoir pH has received only cursory attention in the prior art. Furthermore, previous disclosures relating to minimizing skin irritation from electrotransport devices have concentrated on the active or donor reservoir. However, electrotransport devices apply as much current through the counter electrode as through the donor electrode, and hence, skin irritation due solely to application of electric current also occurs beneath the counter reservoir or counter electrode. In a typical electrotransport device, the area of device/skin contact beneath the counter reservoir is nearly equivalent to the area beneath the donor reservoir. Hence, skin erythema, irritation, and/or damage in the counter reservoir contact area may be similar in magnitude to that in the donor reservoir contact area.

DISCLOSURE OF THE INVENTION

Hence, it is an object of this invention to provide means by which tissue irritation, erythema and/or damage may be reduced or eliminated during and after electrotransport of an agent through a body surface (eg, skin).

It is a further object of the present invention to optimize the pH of a reservoir in an electrotransport device, particularly counter electrode reservoir pH, for purposes of reducing skin irritation during and after transdermal electrotransport drug delivery.

It is still another object of the present invention to reduce the electrical power requirements for an electrotransport device for delivering an agent through a body surface.

Another object of this invention is to provide means by which the electrical resistance to electrotransport agent delivery may be reduced during electrotransport of the agent through a body surface.

A further object of this invention is to improve patient compliance with electrotransport drug administration schedules.

Satisfaction of these objects and other advantages of this invention will become apparent from the electrotransport devices and methods of the present invention. The electrotransport devices contain cathodic and anodic electrodes and cathodic and anodic reservoirs. In one embodiment, the cathodic reservoir pH is maintained below about 4, preferably from about 2 to 4. In another embodiment, the anodic reservoir pH is maintained above about 4, preferably from about 4 to 10.

In a further preferred embodiment, the pH of one or both of the reservoirs is maintained using a suitable buffer. Most preferably, the cathodic reservoir is buffered using a cationic buffer and/or the anodic reservoir is buffered using an anionic buffer. Most preferably, the cathodic and/or anodic electrodes are composed of electrochemically reactive materials, ie, an electrochemically oxidizable anode and an electrochemically reducible cathode, in order to reduce water hydrolysis and the attendant production of hydronium and hydroxyl ions in the anodic and cathodic reservoirs, respectively.

In another embodiment of the present invention, a method of reducing skin resistance and/or erythema during transdermal electrotransport delivery of an agent is presented. One method involves placing the anodic and cathodic reservoirs of an electrotransport delivery device in ion-transmitting relation with a body surface, applying an electrical potential across the reservoirs, and maintaining the cathodic reservoir pH below about 4, preferably from about pH 2 to 4, during electrotransport delivery in order to reduce skin resistance and/or irritation, erythema or damage at the skin site adjacent to the cathodic reservoir. Another method involves placing the anodic and cathodic reservoirs in ion-transmitting relation with a body surface, applying an electrical potential across the reservoirs, and maintaining the anodic reservoir pH above about 4, preferably from about pH 4 to 10, during electrotransport delivery in order to reduce skin resistance and/or irritation, erythema or damage at the skin site adjacent the anodic reservoir.

In accordance with another embodiment of the present invention, a method of avoiding, or at least reducing, skin irritation, erythema and/or damage due to electrotransport agent delivery through the skin is provided. The method involves monitoring for potassium efflux from the skin site through which electric current is applied by the electrotransport delivery device during operation of the device. Once potassium efflux reaches a predetermined value, the operation of the delivery device is altered in a manner designed to avoid, or at least reduce, further skin irritation, erythema and/or damage. Preferably, a potassium sensor is placed in the cathodic electrode assembly in order to monitor potassium efflux from the patient's skin. Once the potassium sensor senses a certain level of potassium efflux, the operation of the device is altered, eg, by reducing the level of current applied by the device or by alerting the patient, eg, through an audible and/or visible alarm. The device may then be removed from the original skin site and placed on an alternate skin site and electrotransport agent delivery thereafter resumed.

BRIEF DESCRIPTION OF THE DRAWINGS

This invention will be described in further detail with reference to the accompanying drawings wherein.

MODES FOR CARRYING OUT THE INVENTION

Figure 1:
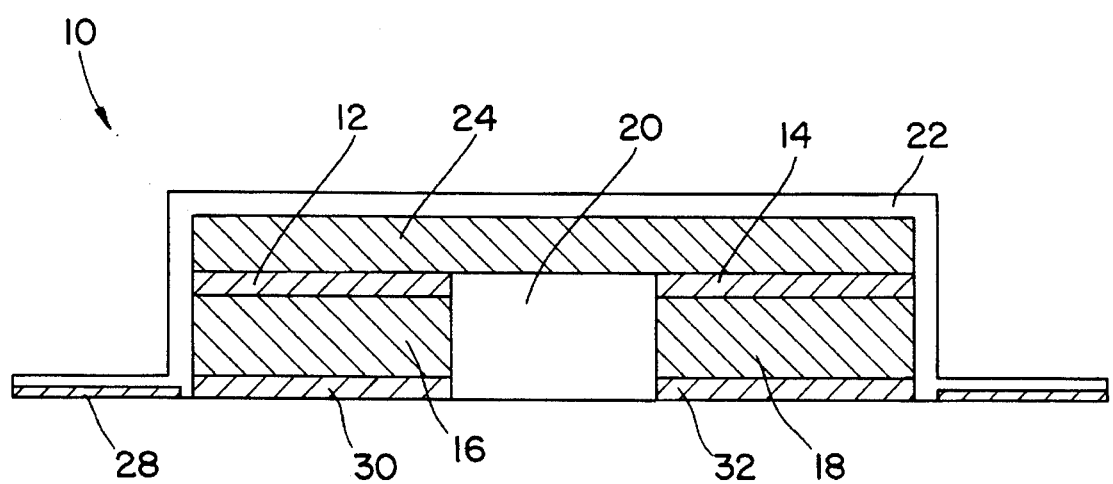
FIG. 1 is a sectional view of one embodiment of an electrotransport device useful in accordance with the present invention.

The present invention may be utilized in a wide variety of electrotransport devices. In general, electrotransport devices have a source of electrical power (eg, one or more batteries) which is, or may be, electrically connected to a donor electrode including a reservoir capable of holding a liquid solution or suspension of the agent to be delivered and a counter electrode including a liquid solution or suspension of an electrolyte salt. One example of an electrotransport device 10 is illustrated in FIG. 1. Device 10 has two electrodes, comprised of electrically conductive materials, referred to herein as a donor electrode 12 and a counter electrode 14. The donor and counter electrodes 12 and 14 are positioned adjacent to, and in electrical contact with, the donor reservoir 16 and the counter reservoir 18, respectively. The donor reservoir 16 contains the agent to be delivered, while the counter reservoir 18 may contain a biocompatible electrolytic salt or another agent to be delivered. An electrical insulator 20 is positioned between (i) the donor electrode 12 and donor reservoir 16 and (ii) the counter electrode 14 and counter reservoir 18. Insulator 20, which may be an air gap or may be composed of a material which neither conducts electrons or ions, prevents device 10 from short-circuiting through a path which does not include the body surface 40 to which device 10 is applied. The device 10 optionally includes a backing layer 22 composed of a liquid impermeable non-conducting material. Device 10 has an electronic circuit, illustrated schematically in FIG. 1 as layer 24, having a DC power source (eg, one or more batteries) therein. Typically, the electronic circuit layer 24 is relatively thin and preferably comprised of electronically conductive pathways printed, painted or otherwise deposited on a thin, flexible substrate such as, for example, a film or polymeric sheet, eg, the electronic circuit layer 24 is a printed flexible circuit. In addition to the power source, the electronic circuit layer 24 may also include one or more electronic components which control the level, waveform shape, polarity, timing, etc. of the electric current applied by device 10. For example, circuit layer 24 may contain one or more of the following electronic components: control circuitry such as a current controller (eg, a resistor or a transistor-based current control circuit), an on/off switch, and/or a microprocessor adapted to control the current output of the power source over time. The outputs of circuit layer 24 are electrically connected to the electrodes 12 and 14 such that each electrode is in electrical contact with an opposite pole of the power source within circuit layer 24. The device adheres to the body surface in this embodiment by means of a peripheral adhesive layer 28. Optionally, the device may contain an in-line adhesive layer, ie, an adhesive layer positioned between the reservoirs 16 and/or 18 and the skin. An in-line adhesive must be composed of an ion-transmitting material, ie, donor agent ions must be capable of penetrating the adhesive layer to reach the body surface. Optional flux control membranes 30 and 32 are positioned between donor reservoir 16 and body surface 40 and between counter reservoir 18 and body surface 40, respectively, in order to limit or control the amount of passive (ie, not electrically assisted) flux of agent to body surface 40.

The device 10 of FIG. 1 is merely one example of an electrotransport device useful in accordance with present invention. The present invention is useful in a wide variety of electrotransport devices, including those devices which are not unitary, ie those which have a power source component and two electrode components, wherein the components are connected only by wiring. An example of a non-unitary or "satellite" device appears in Petelenz et al, U.S. Pat. No. 4,752,285 (See FIG. 6), which is incorporated herein by reference. In addition, the device 10 may contain other features, such as a removable release liner (not shown) on the adhesive layer 28 and/or the body surface-contacting face of the device. Furthermore, certain components in device 10 are unnecessary or optional for practicing the instant invention. For example, if electrodes 12 and 14 are chosen such that a galvanic couple exists, an independent power source in circuit layer 24 may be an optional component. Thus, device 10 of FIG. 1 is presented solely for illustration of one embodiment of the present invention.

If the agent to be delivered is anionic, ie, negatively charged, the cathodic electrode is the donor electrode and the cathodic reservoir is the donor reservoir, containing the agent, and the anodic reservoir is the counter reservoir, containing a biocompatible electrolytic salt. Alternatively, if the agent to be delivered is cationic, ie positively charged, the anodic electrode is the "donor" electrode and the anodic reservoir is the donor reservoir containing the agent to be delivered and the cathodic reservoir is the counter reservoir.

In accordance with one embodiment of the present invention, the pH of the cathodic reservoir, regardless of whether the cathodic reservoir is the donor (ie, agent-containing) or counter (ie, electrolyte-containing) reservoir, is maintained during electrotransport agent delivery at a pH below about 4. By maintaining the cathodic reservoir pH below about pH 4 during electrotransport agent delivery (i) the electrical resistance of the skin site adjacent the cathodic reservoir is reduced and (ii) skin irritation, erythema and/or damage is also reduced. This reduced skin resistance translates into reduced voltage and power requirements needed to drive a particular level of electric current through the body surface. Thus, maintaining the cathodic reservoir pH below about 4 reduces the cost and/or size of the power source. Further, reduced skin irritation, erythema and/or damage results in better acceptance of the treatment regimen by the patient.

Accordingly, patient compliance with prescribed treatment using the electrotransport device is improved.

Preferably, the cathodic reservoir pH is maintained in a range from about 1.4 to about 4, most preferably about 2 to 4. At very low reservoir pH, eg, about a pH of 1, the skin may experience acidic burns. At these high hydronium ion concentrations, the beneficial effect (ie, lower electrical skin resistance) of maintaining the cathodic reservoir at a low pH is outweighed by the damage caused by acid burning. Since irritation, erythema, and/or skin damage may increase at very low reservoir pH, maintaining the cathodic reservoir below a pH of about 1.4 is less preferred.

The pH of the cathodic reservoir may be maintained below about pH 4 by any number of means. In applications where the electrotransport device is operated at low current densities (eg less than about 200 $\mu A/cm^2$) using electrochemically reducible cathode materials such as silver chloride (both of which minimize the formation of hydroxyl ions at the cathode) and/or for short periods of time (eg, <1 hour), it may be sufficient to simply add an acid (eg citric acid) to the cathodic reservoir to maintain the desired pH. However, while acids are effective in achieving a low cathodic reservoir pH, they introduce undesirable competing ions in those instances where the cathodic electrode is the donor electrode. Thus, adding citric acid to a cathodic donor reservoir containing salicylate anions undesirable adds citrate ions which compete with the salicylate ions for delivery into the body. The competing citrate ions also introduce uncertainty in the salicylate delivery rate since it is difficult to predict what percentage of the total applied current is carried by the competing citrate ions.

In applications where the electrotransport agent delivery (i) must be precisely controlled, (ii) is conducted for longer periods of time (eg, >12 hours), (iii) is conducted using cathodic reservoirs having a small volume (pH is a measure of concentration and hence is highly dependant on the volume of the reservoir, with small volume reservoirs being more susceptible to pH changes during operation of the electrotransport device), (iv) is conducted using high current densities, and/or (v) is conducted using a cathode composed of an electrochemically catalytic material (eg, platinum or stainless steel), then the cathodic reservoir is preferably buffered at a pH below about 4. A variety of buffers may be useful in maintaining cathodic reservoir pH below about 4. TABLE 1 lists preferred amino acids and the approximate pH range for cationic behavior. Preferably, these amino acids or combinations thereof are chosen as cationic buffers for the cathodic reservoir.

Preferably, the cathodic reservoir contains at least one cationic buffer. A buffer cation within the cathodic reservoir will tend not to be electrotransported through the skin since anions, and not cations, are predominantly delivered from the cathodic reservoir by electrotransport. A poorly transported buffer is preferred in order to avoid depletion of the buffer from the reservoir as well as any irritation associated with buffer ion being transported into the skin. Amino acids are preferred cationic buffers. Preferably, the counter ion, ie anion, to the buffer cation is chloride. In many cases, the counter anions to the buffer ions are transported into the skin from the cathodic reservoir. Chloride is a preferred counter anion because the skin has a high concentration of chloride ions in its natural state. Hence, use of chloride buffering salts in the cathodic reservoir minimizes irritation potential.

The concentration of buffer required in the reservoir will depend on the properties of the specific buffer selected. Generally, the buffer concentration will range from about 0.01M to about 1.0M. Preferably, the buffer concentration will be about 0.01M to about 0.50M. More preferably, the buffer concentration will be about 0.01M to about 0.20M.

TABLE 1

Cationic Amino Acid Buffers for Cathodic Reservoir

| AMINO ACID | pH RANGE FOR CATIONIC BEHAVIOR | PREFERRED pH RANGE FOR CATIONIC BEHAVIOR |
|---|---|---|
| histidine | 1–5 | 2–4 |
| lysine | 1–4 | 1.5–3.5 |
| arginine | 1–4 | 1.5–3.5 |
| aspartic acid | 1–3 | 2–3 |
| glutamic acid | 1–3.2 | 2–3.2 |
| cysteine | 1–4 | 2–3 |
| tyrosine | 1–4 | 2–3 |
| other amino acids | 1–4 | 2–3.5 |

Alternatively, the cathodic reservoir may be buffered using an anionic or negatively charged buffer, which is electrotransported through the skin, or alternatively, mixtures of a cationic buffer from Table 1 and an anionic buffer from Table 2 may also be used. However, the cationic buffers of Table 1 are preferred, particularly when the cathodic electrode is the donor electrode, since buffer cations will not be electrotransported through the skin. Thus, irritation from the presence of a buffer ion in the skin is minimized, as discussed above. The preferred anionic buffers include those named in TABLE 2.

Other ionic compounds, such as sodium chloride, with little or no buffering capacity may optionally be incorporated into the cathodic reservoir. Such additives may be advantageous in decreasing the potential buffer depletion from the reservoir. A disadvantage of adding sodium chloride to the reservoir, at least in the case where the cathodic reservoir is the agent-containing "donor" reservoir, is that more potentially competing ions, ie ions that compete for electrotransport with the agent to be delivered, are introduced.

TABLE 2

Anionic Acid Buffers for Cathodic Reservoir

| BUFFER | pH RANGE FOR ANIONIC BEHAVIOR | PREFERRED pH RANGE FOR ANIONIC BEHAVIOR |
| --- | --- | --- |
| aspartic acid | 3–5 | 3–4 |
| glutamic acid | 3.2–5 | 3.2–4 |
| citric acid | 1–5 | 2–4 |
| succinic acid | 2–5 | 3–4 |
| phosphoric acid | 1–5 | 2–4 |
| acetic acid | 3.5–5 | 3.5–4 |
| EDTA | 1–5 | 2–4 |
| tactic acid | 2.7–4.5 | 2.7–4 |
| benzoic acid | 3–5 | 3–4 |
| tartaric acid | 1.8–4.5 | 2.3–4 |
| maleic acid | 1–5 | 2–4 |
| fumaric acid | 1.8–5 | 2.3–4 |
| sulfuric acid | 1–3.2 | 1.5–3 |
| formic acid | 1.8–5 | 2.3–4 |
| malic acid | 2.1–5 | 2.6–4 |
| malonic acid | 1.7–5 | 2.1–4 |
| glutamic acid | 3–5 | 3–4 |
| adipic acid | 3–5 | 3–4 |

As an alternative to the addition of either an acid or a buffering agent to the cathodic reservoir in order to maintain the pH below about 4, and preferably within the range of about 2 to 4, the pH of the cathodic reservoir may also be appropriately maintained by operating a suitable secondary electrode of the type, and in a manner, described in Phipps et al U.S. Pat. No. 5,125,894, the disclosure of which is incorporated herein by reference. See in particular column 20, lines 53 to 68; column 28, lines 20 to 68; and column 29, lines 1 to 61 of the Phipps et al U.S. Pat. No. 5,125,894 wherein a secondary electrode composed of a material which can be reversibly oxidized and reduced (eg, iridium oxide) to produce either hydronium ions (in the case of oxidation) or hydroxyl ions (in the case of reduction) in order to control pH in the reservoir. Control of pH can be accomplished, via feedback by providing a pH sensor in the reservoir in communication with the control circuitry for the secondary electrode.

With any of the embodiments described hereinabove wherein the pH of the cathodic reservoir is appropriately maintained, a potassium sensor may optionally be incorporated into the cathodic reservoir to monitor for potassium ion efflux from the skin into the cathodic reservoir. Excessive potassium ion efflux from the skin has been found to occur concurrently with skin irritation and/or erythema accompanying transdermal electrotransport agent delivery. Since potassium is a cation, the electrotransport-driven efflux from the skin tends to deliver potassium ions into the cathodic reservoir. The potassium efflux can therefore be monitored directly by measuring the amount of potassium in the cathodic reservoir or the rate of change of potassium concentration in the cathodic reservoir. We have observed that potassium effluxes of less than about 5 µg/cm$^2$.h correlate with very little skin irritation or redness whereas potassium effluxes of greater than about 10 µ/cm$^2$.h correspond to moderate levels of skin irritation and redness. When the potassium concentration of the cathodic reservoir exceeds a predetermined value, eg, a concentration which corresponds to a level of potassium efflux which is a predecessor of skin irritation, erythema and/or damage, the controller component of the electrotransport system can be made to respond so that the electrotransport agent delivery is either modified or terminated. The response by the controller can take several forms, including (i) signalling the patient to turn off the electrotransport device, remove the device and/or move the site of application of the electrotransport device, (ii) automatic termination, interruption or reduction of the level of electric current applied by the device, and/or (iii) operation of a secondary electrode of the type described in Phipps et al U.S. Pat. No. 5,125,894 to alter the pH of the cathodic and/or anodic reservoirs.

In accordance with another embodiment of the present invention, the pH of the anodic reservoir is maintained during electrotransport agent delivery above about 4, and preferably at a pH from about 4 to about 10. By maintaining the anodic reservoir pH above about pH 4 during electrotransport agent delivery, (i) the electrical resistance of the skin site adjacent the anodic reservoir is reduced, and (ii) skin irritation, erythema and/or damage to the skin site adjacent to the anodic reservoir is also reduced. This reduced skin resistance translates into reduced voltage and power requirements needed to drive a particular level of electric current through the body surface. Thus, maintaining the anodic reservoir pH above about 4 reduces the cost and/or size of the power source.

The pH of the anodic reservoir may be maintained above pH 4 by any number of means. In applications where the electrotransport device is operated at low current densities (eg, less than 200 µA/cm$^2$) using electrochemically oxidizable anode materials such as silver (both of which minimize the formation of hydronium ions at the anode) and/or for short periods of time (eg, less than 1 hour), it may be sufficient to simply add a weak acid (eg, a carboxylic acid) or a base to the anodic reservoir to maintain the desired pH. However, while weak acids or bases are effective in achieving an appropriate anodic reservoir pH, they introduce undesirable competing ions in those instances where the anodic electrode is the donor electrode. Thus, adding a carboxylic acid, or sodium hydroxide, to an anodic donor reservoir containing lidocaine cations undesirably adds hydronium ions, or sodium ions, respectively, which ions compete with the lidocaine/sodium ions for delivery into the body. The competing hydronium ions also introduce uncertainty in the lidocaine delivery rate since it is difficult to predict what percentage of the total applied current is carried by the competing hydronium ions.

In applications where the electrotransport agent delivery (i) must be precisely controlled, (ii) is conducted for longer periods of the time (eg, >12 hours), (iii) is conducted using an anodic reservoir having a small volume (pH is measure of concentration and hence is highly dependent on the volume of the reservoir, with small volume reservoirs being more susceptible to pH changes during operation of the electrotransport device), (iv) is conducted using high current densities, and/or (v) is conducted using an anode composed of an electrochemically catalytic material (eg, platinum or stainless steel), the anodic reservoir is preferably buffered at a pH above about 4. More preferably, the buffer has a relatively low anodic electrotransport rate through the skin. Preferred buffers include amino acids exhibiting anionic behavior at a pH greater than 4, as listed in TABLE 3. Of the amino acids, cysteine, histidine, and tyrosine are most preferred.

TABLE 3

Anionic Amino Acid Buffers for Anodic Reservoir

| AMINO ACID | pH RANGE FOR ANIONIC BEHAVIOR | PREFERRED pH RANGE FOR ANIONIC BEHAVIOR |
|---|---|---|
| histidine | 7.5–10.5 | 7.5–10 |
| cysteine | 7–12 | 7.5–11.5 |
| tyrosine | 7.8–11.4 | 8.3–10.9 |
| lysine | 9.7–11.8 | 9.7–11.3 |
| arginine | 10.8–13 | 10.8–12 |
| aspartic acid | 3–5.2 | 4–4.6 |
|  | 8.5–11.1 | 9.1–10.5 |
| glutamic acid | 3.2–5.5 | 4–5 |
|  | 8.4–11 | 8.9–10.4 |
| other amino acids | 8–12 | 9–11 |

Other anodic reservoir buffers include certain zwitterions, examples of which are listed in TABLE 4. Preferred zwitterions are N-2-Hydroxyethylpiperazine-N'-2-ethane sulfonic acid (HEPES) and 2-(N-Morpholino)-propane sulfonic acid (MOPS).

TABLE 4

Zwitterion Buffers for Anodic Reservoir

| ZWITTERION (Abbreviation) | ZWITTERION (Full Chemical Name) | pH RANGE FOR ANIONIC BEHAVIOR | PREFERRED pH RANGE FOR ANIONIC BEHAVIOR |
|---|---|---|---|
| MES | 2-(N-morpholino)-ethane sulfonic acid | 4.8–7.4 | 5.4–6.8 |
| PIPES | 1,4-piperazine-bis-(ethanesulfonic acid) | 5–7.6 | 5.6–7 |
| ADA | N-2-acetamido iminodiacetic acid | 5.3–7.9 | 5.9–7.3 |
| ACES | N-2(2-acetamido)-2-aminoethane sulfonic acid | 5.6–8.2 | 6.2–7.6 |
| BES | N,N-bis(2-hydroxyethyl)-2-aminoethane sulfonic acid | 5.9–8.4 | 6.4–7.8 |
| MOPS | 2-(N-morpholino)-propane sulfonic acid | 5.9–8.5 | 6.5–7.9 |
| TES | N-tris(hydroxymethyl) methyl-2-aminoethane sulfonic acid | 6.2–8.8 | 6.8–8.2 |
| HEPES | N-2-hydroxyethylpiperazine-N'-2-ethane sulfonic acid | 6.2–8.8 | 6.8–8.2 |
| EPPS | 4-(2-hydroxyethyl)-1-piperazine propane sulfonic acid | 6.7–9.3 | 7.3–8.7 |
| TAPS | N-tris(hydroxymethyl) | 7.1–9.7 | 7.7–9.1 |

TABLE 4-continued

Zwitterion Buffers for Anodic Reservoir

| ZWITTERION (Abbreviation) | ZWITTERION (Full Chemical Name) | pH RANGE FOR ANIONIC BEHAVIOR | PREFERRED pH RANGE FOR ANIONIC BEHAVIOR |
|---|---|---|---|
| | methyl-2-aminopropane sulfonic acid | | |
| CHES | 2-cyclohexylamino-1-ethane sulfonic acid | 8.2–10.8 | 8.8–10.2 |
| CAPS | 3-cyclohexylamino-1-propanesulfonic acid | 9.1–11.7 | 9.7–11.1 |

In addition, acids having a pKa between 2 and 10 are suitable anionic buffers for the anodic reservoir. Examples of such acids can be found in TABLE 5. The preferred anionic acid buffers include citric acid, succinic acid, phosphoric acid, maleic acid, and malonic acid.

TABLE 5

Anionic Acid Buffers for Anodic Reservoir

| BUFFER | ANIONIC pH RANGE | PREFERRED ANIONIC pH RANGE |
|---|---|---|
| citric acid | 3–8 | 4–7 |
| succinic acid | 3–7.5 | 4–6.5 |
| phosphoric acid | 3–9 | 4–8 |
| maleic acid | 3–7.5 | 4–7 |
| malonic acid | 3–7.5 | 4–7 |
| acetic acid | 3–6 | 4–5.5 |
| boric acid | 8–10.5 | 8.5–9.9 |

TABLE 5-continued

Anionic Acid Buffers for Anodic Reservoir

| BUFFER | ANIONIC pH RANGE | PREFERRED ANIONIC pH RANGE |
|---|---|---|
| EDTA | 3–12 | 4–11 |
| lactic acid | 3–5 | 4–5 |
| benzoic acid | 3.5–5.5 | 4–5.5 |
| tartaric acid | 3–5.6 | 4–5.1 |
| fumaric acid | 3–6 | 4–5.1 |
| formic acid | 3.5–5 | 4–4.5 |
| malic acid | 3–6.3 | 4–5.8 |
| carbonic acid | 5.2–7.8 | 5.6–7.1 |
| glutamic acid | 3–7 | 4–6.5 |
| adipic acid | 3–7 | 4–6.5 |

Alternatively, the anodic reservoir may be buffered using a buffer which has a relatively high anodic electrotransport rate, ie, a cationic or positively charged buffer which buffers the anodic reservoir at a pH greater than about 4, preferably at a pH of about 4 to 10. Suitable cationic buffers include bases having at least one pKa between 2 and 10, certain other bases, and amino acids displaying cationic behavior at the reservoir pH. Examples of cationic buffers suitable for the anodic reservoir are listed in TABLE 6. In addition, mixtures of an acid from Table 5 and a base from Table 6 may also be used to buffer the anodic reservoir. However, the buffers of Table 5 are preferred over the buffers of Table 6, particularly when the anodic electrode is the donor electrode since the Table 5 buffers do not compete with the agent for delivery into the body. The preferred bases for use in the anodic reservoir include tromethamine, triethanolamine and imidazole.

TABLE 6

Cationic Amino Acids for the Anodic Reservoir

| BASE BUFFER | pH RANGE FOR CATIONIC BEHAVIOR | PREFERRED pH RANGE FOR CATIONIC BEHAVIOR |
|---|---|---|
| tromethamine | 6.8–9.3 | 7.3–8.8 |
| triethanolamine | 6.5–9 | 7–8.5 |
| imidazole | 5.8–8.2 | 6.3–7.7 |
| ammonia | 8–10.5 | 8.5–10 |
| ethanolamine | 8.2–10.8 | 8.8–10.2 |
| diethanolamine | 7.6–10.2 | 8.2–9.6 |
| histidine | 3–7.5 | 4–7.5 |
| lysine | 7.7–9.7 | 8.2–9.7 |
| arginine | 7.8–10.8 | 8.3–10.8 |

The concentration of buffer required in the anodic reservoir, as in the cathodic reservoir, will depend on the properties of the specific buffer selected. Generally, the buffer concentration in the anodic reservoir will range from about 0.01M to about 1.0M. Preferably, the buffer concentration will be about 0.01M to about 0.50M. More preferably, the buffer concentration will be about 0.01M to about 0.20M.

As an alternative to the addition of either a weak acid, a base, or a buffering agent to the anodic reservoir in order to maintain the pH above about 4, and preferably in the range of about 4 to 10, the pH of the anodic reservoir may also be appropriately maintained by operating a suitable secondary electrode of the type, and in a manner, described in Phipps et al U.S. Pat. No. 5,125,894, discussed earlier herein.

With any of the embodiments described hereinabove wherein the pH of the anodic reservoir is appropriately maintained, a potassium sensor may optionally be incorporated into the cathodic reservoir to monitor for potassium ion efflux from the skin into the cathodic reservoir. When the potassium concentration of the reservoir exceeds a value which corresponds to a predetermined potassium efflux, the controller component of the electrotransport system can be made to respond as described hereinearlier.

In those cases where competition from buffer ions/counterions must be minimized or eliminated, the buffer added to the anodic or cathodic reservoir is preferably polymeric. Examples of polymeric buffers include, without limitation, those listed in TABLE 7. TABLE 7 also lists pH ranges for anionic and cationic behavior for the listed buffers. The polymeric buffers used in the cathodic reservoir are preferably those displaying polymer cationic behavior at a pH of less than about 4. The preferred polymeric buffers for the anodic reservoir are those in which the polymer is anionic at a pH greater than about 4.

TABLE 7

| POLYMERIC BUFFER | ANIONIC pH RANGE | CATIONIC pH RANGE |
| --- | --- | --- |
| polyacrylic acid | 3–8 | |
| polymethacrylic acid | 3–8 | |
| poly(styrene maleic anhydride) | 3–8 | |
| methacrylate/divinyl benzene copolymers[1] | 3–8 | |
| poly(2-acrylamido-2-methylpropane sulfonate) | 1–5 | |
| copolymers of acrylic acid and long chain acrylate esters[2] | 3–8 | |
| poly(methylvinyl ether-maleic acid)[3] | 2–8 | |
| vinylpyrrolidone/ quaternized dimethylamino- ethylmethacrylate copolymers[4] | | 7–10 |
| vinylcaprolactam/ vinylpyrrolidone/ dimethylamino ethylmethacrylate terpolymers[5] | | 7–10 |
| polyvinylpyridine | | 6–9 |
| methacrylate/divinyl benzene copolymers[6] | | 6–9 |

[1] Amberlite IRP-64, an insoluble, weakly acidic, cation exchange resin sold by Rohm and Haas Co., Philadelphia, PA.
[2] Pemulen polymeric emulsifiers, sold by B. F. Goodrich Co., Specialty Polymers & Chemicals Division, Brecksville, OH.
[3] Gantrez S95 and S97, made and sold by ISP Technologies, Inc. of Wayne, NJ.
[4] Gafquat 755 and 755N, made and sold by ISP Technologies, Inc. of Wayne, NJ.
[5] Gaffix VC-713, made and sold by ISP Technologies, Inc. of Wayne, NJ.
[6] Amberlite IRP-88, a cross-linked, weakly acidic, cation exchange resin sold by Rohm and Haas Co. of Philadelphia, PA.

The pH of a given reservoir affects primarily the skin directly adjacent (eg, in contact with) that reservoir. Thus, the cathodic reservoir pH affects the irritation and electrical resistance of the skin site adjacent to the cathodic reservoir, while the anodic reservoir pH affects the irritation and electrical resistance of the skin site adjacent to the anodic reservoir. Accordingly, this invention contemplates those devices in which (i) the cathodic reservoir pH is maintained below 4, (ii) the anodic reservoir pH is maintained above 4 and (iii) both reservoir pH's are appropriately maintained. However, in the preferred practice of the invention, both the anodic reservoir is maintained at a pH above about 4, and the cathodic reservoir is maintained at a pH below about 4. More preferably, both the anodic and cathodic reservoirs are buffered at the appropriate pH.

As mentioned herein earlier, the pH of the donor (drug-containing) reservoir is in many cases not subject to adjustment in accordance with the ranges specified herein since the solubility of the drug in the liquid solvent may be insufficient at those pH ranges. Thus, the present invention has particular utility when used to adjust the pH of the counter reservoir from which no drug is being delivered. Thus, in cases where a cationic drug is being delivered from an anodic reservoir, the present invention is particularly useful in maintaining the pH of the counter cathodic reservoir below about 4, preferably from about pH 2 to 4. Conversely, when delivering an anionic drug from the cathodic reservoir, the present invention is particularly useful in adjusting the pH of the counter anodic counter reservoir to a pH above about 4, preferably from about pH 4 to 10. Even in those cases where the pH of the donor reservoir cannot be adjusted in accordance with the ranges disclosed herein, the electrical resistance and irritation of the skin which is adjacent the counter reservoir can still be substantially reduced. Thus, at the very least, the present invention provides a method for (i) reducing the electrical resistance of at least one of the two skin sites through which electric current is applied during electrotransport agent delivery; and (ii) reducing or eliminating at least about one half of the skin irritation potential (ie, the skin site beneath the counter electrode reservoir) due to electrotransport agent delivery. Of course, it is most preferred that the pH of both the donor and counter electrode reservoirs be appropriately maintained in order to reduce the electrical resistance and the irritation potential for both the skin site adjacent the counter electrode reservoir and the skin site adjacent the donor electrode reservoir.

In the situation where the agent is delivered primarily by electromigration, then the pH of the donor electrode reservoir can be appropriately maintained as described herein as long as at that pH, at least about 50% of the agent to be delivered is charged. Those skilled in the art will clearly appreciate that for agents being delivered primarily by electromigration, the pH of the donor reservoir can be set to minimize electrical resistance and irritation potential as taught herein only if the agent being delivered has one or more appropriate pK's, ie, a pK which allows the donor reservoir pH to be set as taught herein (ie, anodic donor reservoir pH above 4 and/or cathodic donor reservoir pH below 4) and which pH allows the agent to exist in a state wherein at least 50% of the agent has a charge of the appropriate sign (±). For example, morphine, a narcotic analgesic, has a pK of 8.3 at 25° C. Thus, in a solution of morphine with a pH of 8.3, 50% of the morphine is positively charged and 50% is uncharged. Accordingly, the appropriate pH range for the anodic morphine-containing donor electrode in an electrotransport device for delivering morphine primarily by electromigration is pH 4 to 8.3.

The donor reservoir and counter reservoir can be formed of any material adapted to absorb and hold a sufficient quantity of liquid therein in order to permit transport of agent therethrough by electrotransport. For example, gauzes, pads or sponges composed of cotton or other absorbent fabric, both natural and synthetic, may be used. Preferably, the matrices of the reservoirs are composed, at least in part, of hydrophilic polymer material. Hydrophilic polymers are typically preferred because water is the preferred ion transport medium, and hydrophilic polymers have a relatively high equilibrium water content. More preferably, the matrices of the reservoirs are solid polymer matrices composed, at least in part, of an insoluble hydrophilic polymer. Insoluble hydrophilic polymer matrices are preferred for structural reasons over soluble hydrophilic polymers, ie reservoir shape may be more easily retained upon hydration of a hydrophilic polymer matrix composed of a water insoluble polymer compared to a matrix composed of a water soluble polymer or gel.

The matrices can be crosslinked with the agent in place, such as with a silastic matrix, or the polymers can be prefabricated and sorbed with the components from solutions as is the case with cellulose, woven fiber pads and sponges. The reservoirs can alternately be a gel matrix structure, formed similarly to the polymeric matrix structure, wherein the gel is formed of a hydrophilic polymer which is swellable or soluble in water. Such polymers can be blended with the components in any ratio, but preferably represent from a few percent up to about 50 percent by weight of the reservoir. The polymers can be linear or cross-linked. Suitable hydrophilic polymers include copolyesters such as HYTREL (DuPont De Nemours & Co., Wilmington, Del.), polyvinylpyrrolidones, polyvinyl alcohol, polyethylene oxides such as POLYOX (Union Carbide Corp.), CARBOPOL (BF Goodrich of Akron, Ohio), blends of polyoxyethylene or polyethylene glycols with polyacrylic acid such as POLYOX blended with CARBOPOL, polyacrylamide, KLUCEL, cross-linked dextran such as SEPHADEX (Pharmacia Fine Chemicals, AB, Uppsala, Sweden), WATER LOCK (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxylethyl methacrylate (National Patent Development Corp.), natural gums, chitosan, pectin, starch, guar gum, locust bean gum, and the like, along with blends thereof. This list is merely exemplary of the materials suited for use in this invention.

Optionally, the matrices of the reservoirs may contain a hydrophobic polymer for enhanced structural rigidity or improved bonding characteristics. Preferably the hydrophobic polymer is heat fusible, in order to improve the lamination of the reservoirs to adjacent components, such as an insulating material or a rate-controlling membrane. Suitable hydrophobic polymers for use in the reservoir matrices include, but are not limited to, polyisobutylenes, polyethylene, polypropylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butyl acryl amide, itaconic acid, N-branched alkyl maleamic acids wherein the alkyl group has 10–24 carbon atoms, glycol diacrylates, and blends thereof. Most of the above-mentioned hydrophobic polymers are heat fusible.

The reservoir matrices may be a polymeric matrix structure formed by blending the desired agent, drug, electrolyte, or other component(s), with an inert polymer by processes such as melt blending, solvent casting, or extrusion. The donor reservoir contains an agent to be delivered, while the counter reservoir may contain an electrolyte, eg a water soluble biocompatible salt, such as sodium chloride. In addition to the delivery agent and electrolyte, the reservoirs may also contain other conventional materials such as water, permeation enhancers, dyes, pigments, inert fillers, and the like.

The electrodes of the present invention are composed of an electrically conductive material such as a metal. For example, the electrodes may be formed from metal foil, metal screen, metal deposited or painted on a suitable backing, calendaring, film evaporation, or by embedding a metal powder in a binder matrix. Examples of suitable metals include silver, zinc, silver chloride, aluminum, platinum, stainless steel, gold, and titanium. For example, the anodic electrode may be composed of silver, while the cathodic electrode may be composed of silver chloride.

Further, if the electrodes are selected from dissimilar materials, a galvanic couple may be formed. A galvanic couple may provide all or at least part of the electrical potential required to operate the device. Exemplary of such a galvanic couple are a pair of electrodes formed from silver and zinc chloride.

Alternatively, the electrodes may be formed of a polymer matrix containing a conductive filler such as a metal powder, powdered graphite, carbon fibers, or other electrically conductive filler material. The polymer-based electrodes may be produced by mixing the conductive filler in a polymer matrix, preferably hydrophobic in order to minimize interaction with any water present in the reservoirs.

Preferably, the electrodes of the present invention are comprised of electrochemically reactive materials, ie, the anode is composed of an electrochemically oxidizable material (eg, silver) and/or the cathode is composed of an electrochemically reducible material (eg, silver chloride). Electrochemically reactive electrode materials are preferred because their use minimizes water hydrolysis, which results in the production of hydroxyl ($OH^{31}$) and hydronium ($H^+$) ions, which can alter reservoir pH and also introduces competing ions in the donor reservoir. Hydroxyl or hydronium ions may be transported into the skin causing a high or low, respectively, pH in the skin, thereby causing erythema, irritation, and/or damage. The preferred electrochemically reactive electrodes are the aforementioned silver and silver chloride electrodes.

This invention has utility in connection with the delivery of agents within the broad class deliverable through body surfaces, including skin, mucosa, and nails. The expressions "drug" and "agent" are used interchangeably herein and are intended to have their broadest interpretation as any substance which is delivered to a living organism to produce a desired, usually beneficial, effect. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary, anticholinergics, antiulceratives such as ranitidine, sympathomimetrics, xanthine derivatives, cardiovascular preparations including calcium channel blockers such as nifedipene, beta-blockers, beta-agonists such as dobutamine and ritodrine, antiarrythmics, antihypertensives such as atenolol, ACE inhibitors such as enalapril, benzodiazepine antagonists such as flumazenil, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other macromolecules. These macromolecular substances typically have a molecular weight of at least about 300 daltons, and more typically a molecular weight in the range of about 300 to 40,000 daltons. Specific examples of peptides, and proteins and macromolecules in this size range include, without limitation, LHRH, LHRH analogs such as buserelin, gonadorelin, napharelin and leuprolide, GHRH, GHRF, insulin, insulotropin, heparin, calcitonin, octreotide, endorphin, TRH, NT-36 (chemical name: N=[[(s)-4-oxo-2-azetidinyl]carbonyl ]-L-histidyl-L-prolinamide), liprecin, pituitary hormones (eg, HGH, HMG, HCG, desmopressin acetate, etc.), follicle luteoids, αANF, growth factors such as growth factor releasing factor (GFRF), βMSH, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirulog, hyaluronidase, interferon, insulin-like growth factors, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neuropeptide Y, neurotrophic factors, oligodeoxynucleotides and their analogues such as antisense RNA, antisense DNA and anti-gene nucleic acids, opiate peptides, colony stimulating factors, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombinant), and TGF-beta.

Having thus generally described the invention, the following examples will illustrate how the invention may be utilized to accomplish effective transdermal electrotransport agent delivery with reduced skin resistance and reduced skin irritation, erythema and/or damage.

EXAMPLE I

In this set of experiments, sodium phosphate buffer (ie, negatively charged phosphate buffer) was added to the cathodic reservoir and various positively charged buffers having chloride counter ions were added to the anodic reservoir. The pH at the cathodic reservoir was varied from 1.35 to 8.17. The purpose of these experiments was to study the effect of reservoir pH on skin irritation/erythema and skin resistance during the application of an electric current, ie, current carried by the movement of ions, through the skin. Since many drugs have at least some potential to irritate the skin upon contact therewith, the only ionic species added to the anodic and cathodic reservoirs were the buffering agents themselves. Hence, no drug was placed in the reservoirs in these Examples. Delivery of drug from the reservoirs is not necessary to study the effects of reservoir pH on the skin since any mobile ionic species can be used to study the effects of electric current through skin.

The electrotransport device had a silver foil anode and a silver chloride cathode. The reservoir gel (ie, both the anodic and cathodic gels) sizes were each approximately 200 µL and had a skin contacting surface area of about 1.25 cm$^2$. For pH 1.35, 1.78, and 1.86, the reservoir gels contained about 0.15M phosphoric acid, 3% by weight hydroxyethyl cellulose, NaOH q.s. to the desired pH, and q.s. water. The 0.15M phosphoric acid was replaced with 0.15M monobasic sodium phosphate for the other pH values examined.

Experiments were performed in vivo on hairless guinea pigs. Both the anodic reservoir and the cathodic reservoir were applied to the backs of the guinea pigs using an adhesive overlay. The two reservoirs were generally spaced about 5 to 7.5 cm apart. The electrodes were connected to a DC power source which supplied a constant current of 0.125 mA (ie, current density of 0.1 mA/cm$^2$). Current was applied for 30 minutes, after which time the electrodes were disconnected from the power source and the gels were removed from the guinea pigs. The skin resistance measurements were made by recording the applied voltage after 5 minutes of applying 0.125 mA of current. Skin resistance (R) values (KOhms.cm$^2$) were calculated by multiplying the measured voltage (V) across the electrodes by the surface area (A) of the contact (ie, 1.25 cm$^2$) and dividing that product by the applied current (I) (ie, 0.1 mA) in accordance with the following equation: $R = VA/I$. Skin irritation measurements were taken about 5 minutes after removal of the electrodes from the skin. Each data point represents an average of the measurements taken from four skin samples, each sample from a different guinea pig.

Quantitative skin irritation (α) measurements were obtained from color measurements generated by a Minolta Chroma Meter Model No. CR 200 (sold by Minolta Camera Corp., Ltd., Osaka, Japan) for this and all subsequent EXAMPLES. The Minolta Chroma Meter is a portable tristimulus color analyzer which converts all colors within the range of human perception into a numerical code using the L*a*b* color notation system. L* (luminance) expresses brightness on the black-white axis; a*, hue on the red-green axis; and b*, chroma on the yellow-blue axis so that a specific numerical code enables an exact color description of an object. The numerical values for α are generated by the Minolta Chroma Meter and have no particular units. The Minolta Chroma Meter utilizes a numerical range of −60 (green) to +60 (red) for a* hue. Typically, human skin ranges from 0 to 10 on the a* hue scale. An α value of 1 to 2 represents a slight redness or erythema; an α value of 3.5 to 4.5 represents a moderate redness or erythema; and an α value of above 7 represents severe redness or erythema. The measurement of skin irritation for these tests is given as α, which is defined herein as the difference of the mean a* reading for the electrotransport-treated samples minus the mean a* reading for the untreated samples, ie α=a*$_{treated}$−a*$_{untreated}$. Minolta measurements were made by taking the mean a* value of three readings at adjacent untreated sites and subtracting that value from the mean of three readings taken at the treated site. Since changes in redness intensity were made from the a* reading, only a* values were employed for the purposes of skin site checks following electrode removal.

Figure 2:
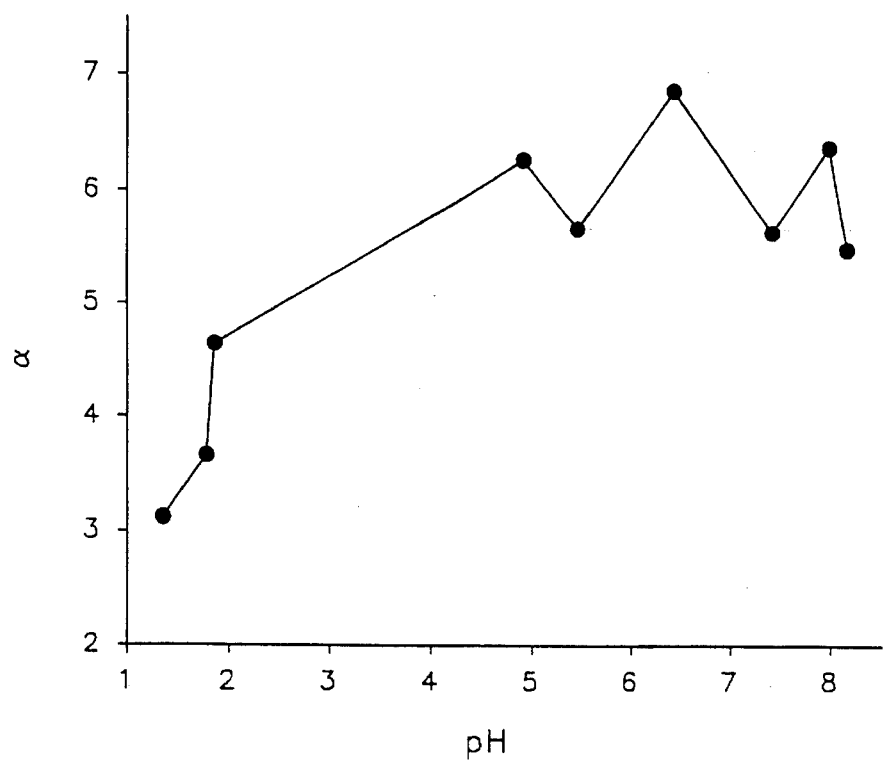
FIGS. 2 and 3 are graphs of skin irritation ($\alpha$) and skin resistance (R), respectively, as a function of cathodic reservoir pH.
Figure 3:
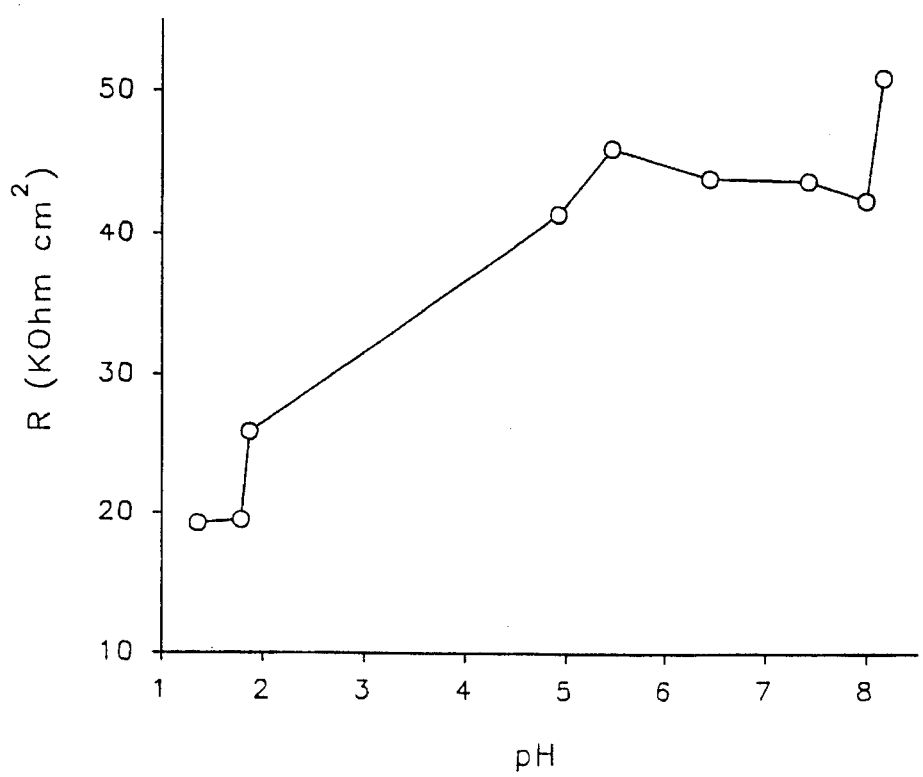
Figure 4:
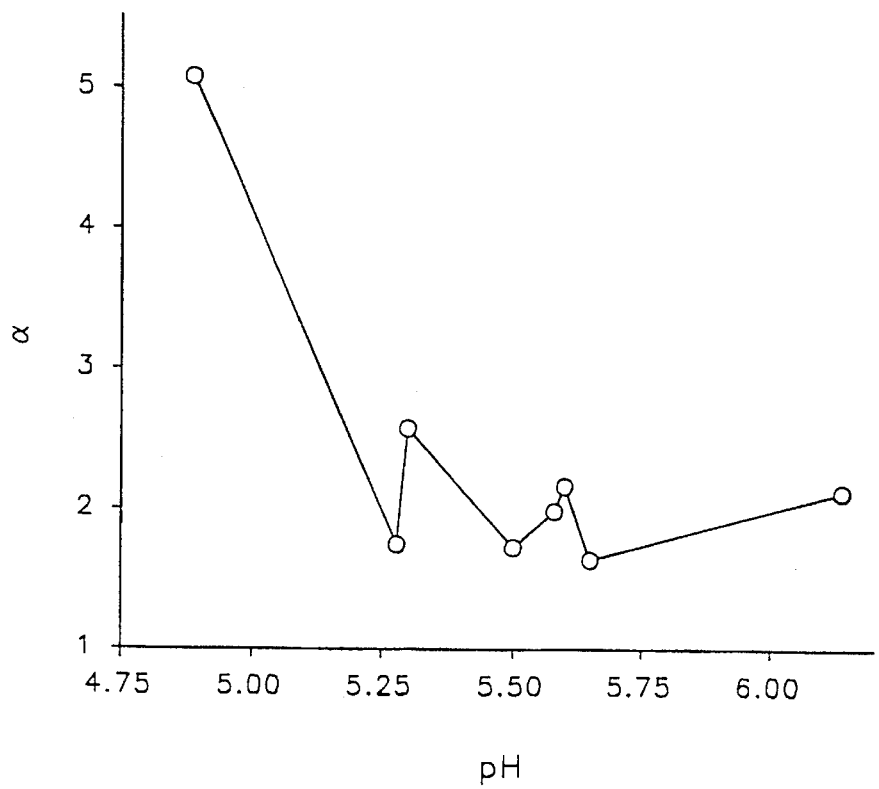
FIGS. 4 and 5 are graphs of skin irritation ($\alpha$) and skin resistance (R), respectively, as a function of anodic reservoir pH.
Figure 5:
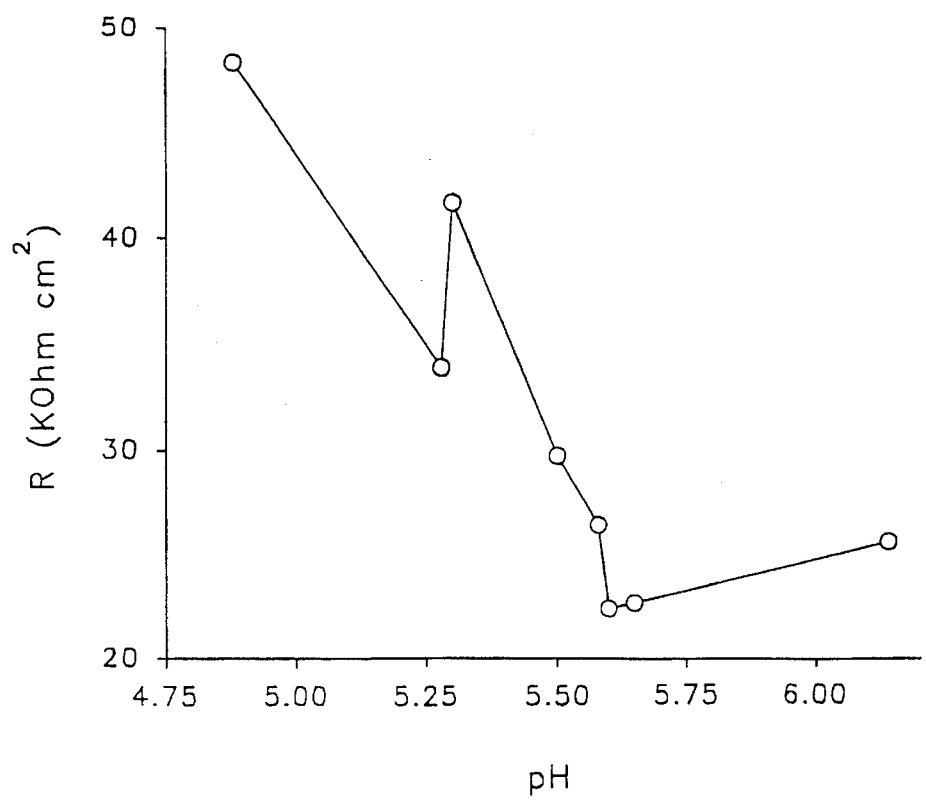

A skin irritation value (α) and skin resistance (R), were tabulated for each pH value studied. Skin irritation and skin resistance as a function of pH are listed for the cathodic reservoir in TABLE 8 and for the anodic reservoir in TABLE 9. FIGS. 2 and 4 illustrate a plot of skin irritation versus pH for the cathodic and anodic reservoirs, respectively. FIGS. 3 and 5 illustrate a plot of skin resistance versus pH for the cathodic and anodic reservoirs, respectively.

TABLE 8

| Cathodic Reservoir pH | Skin Resistance (R) (KOhms · cm$^2$) | Skin Irritation (α) |
| --- | --- | --- |
| 1.35 | 19.3 | 3.1 |
| 1.78 | 19.5 | 3.7 |
| 1.86 | 25.9 | 4.6 |
| 4.92 | 41.4 | 6.3 |
| 5.47 | 46.1 | 5.7 |
| 6.45 | 44.0 | 6.9 |
| 7.42 | 43.8 | 5.6 |
| 8.00 | 42.4 | 6.4 |
| 8.17 | 51.1 | 5.5 |

TABLE 9

| BUFFER | ANODIC RESERVOIR pH | SKIN RESISTANCE (KOhms · cm$^2$) | SKIN IRRITATION (α) |
| --- | --- | --- | --- |
| 0.15M calcium chloride dehydrate | 4.88 | 48.3 | 5.1 |
| 0.15M triethanolamine hydrochloride | 5.28 | 33.9 | 1.7 |
| 0.15M magnesium chloride heptahydrate | 5.3 | 41.7 | 2.6 |
| 0.15M diethanolamine hydrochloride | 5.5 | 29.8 | 1.7 |
| 0.15M ammonium chloride | 5.58 | 26.4 | 2.0 |
| 0.15M ethanolamine hydrochloride | 5.6 | 22.4 | 2.2 |
| 0.15M potassium chloride | 5.65 | 22.7 | 1.6 |
| 0.15M sodium chloride | 6.14 | 25.6 | 2.1 |

The compounds used to adjust the pH of the anodic reservoirs (ie, the Table 9 compounds) were cations which tend to be delivered into the skin by electromigration. At least one of these cations (magnesium; see third line of Table 8) is known to be skin irritating. Thus, the skin irritation (α) value for magnesium chloride heptahydrate may be higher (ie, higher than triethanolamine HCl at a similar pH) due to the irritating effect of magnesium ions.

As TABLE 8 and FIGS. 2–3 illustrate, cathodic reservoir pH values of less than about pH 4, and particularly at pH's of about 2, resulted in lower skin resistance and less skin irritation compared to cathodic reservoir pH's ranging from about 5 to 8. Similarly, TABLE 9 and FIGS. 4–5 indicate that high pH, ie greater than about pH 4 to about 5, at the anodic reservoir results in low skin resistance and low skin irritation.

EXAMPLE II

These experiments involved the use of histidine, lysine, and arginine, all positively charged buffers in the form of chloride salts, in the cathodic reservoir and citric acid, monobasic sodium phosphate, and boric acid, all negatively charged buffers in the form of sodium salts in the anodic reservoir. All reservoir compositions contained about 3% by weight hydroxypropyl cellulose (HPC) and q.s. water. Either HCl or NaOH were added q.s. to achieve the desired pH. The other conditions were the same as described in EXAMPLE I.

Skin resistance (R) and skin irritation (α) as a function of pH are listed (i) in TABLE 10 for the cathodic reservoirs buffered with L-lysine or L-histidine; (ii) in TABLE 11 for the anodic reservoir buffered with citric acid, boric acid, or monobasic sodium phosphate, (iii) in TABLE 12 for the cathodic reservoirs buffered with L-histidine, L-lysine, or L-arginine, and (iv) in TABLE 13 for the cathodic reservoirs buffered with phosphoric acid and monobasic sodium phosphate.

Figure 6:
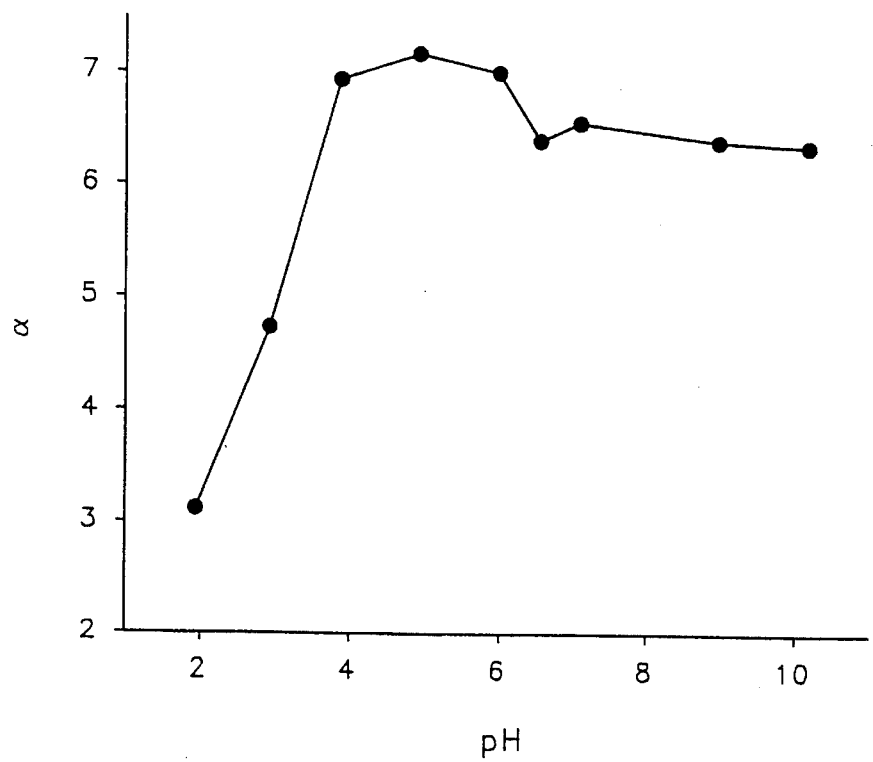
FIGS. 6 and 7 are graphs of skin irritation ($\alpha$) and skin resistance (R), respectively, as a function of cathodic reservoir pH.
Figure 7:
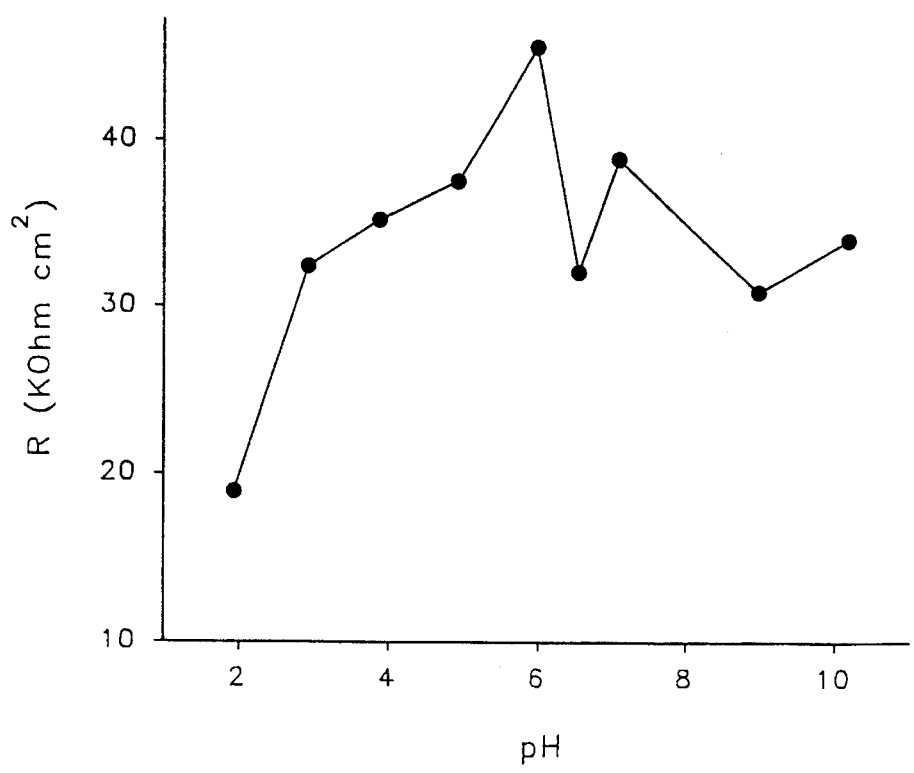
Figure 8:
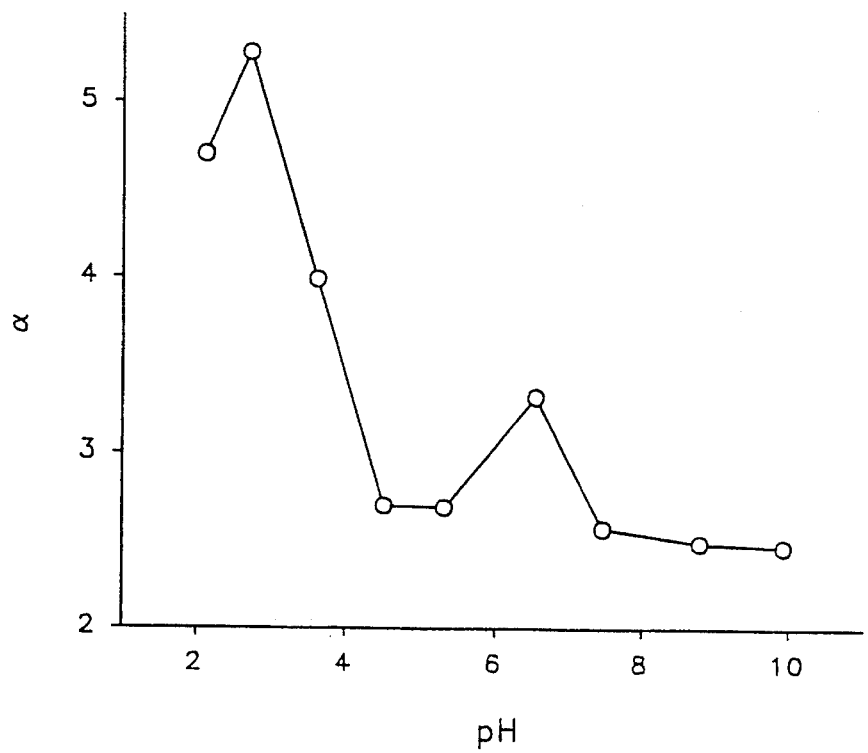
FIGS. 8 and 9 are graphs of skin irritation ($\alpha$) and skin resistance (R), respectively, as a function of anodic reservoir pH.
Figure 9:
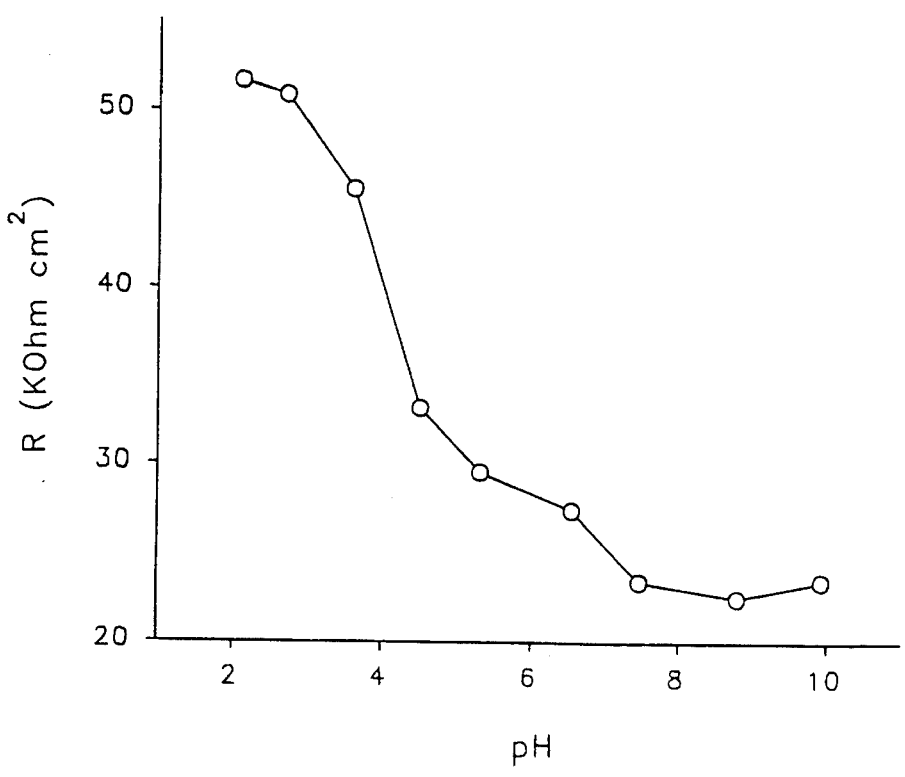
Figure 10:
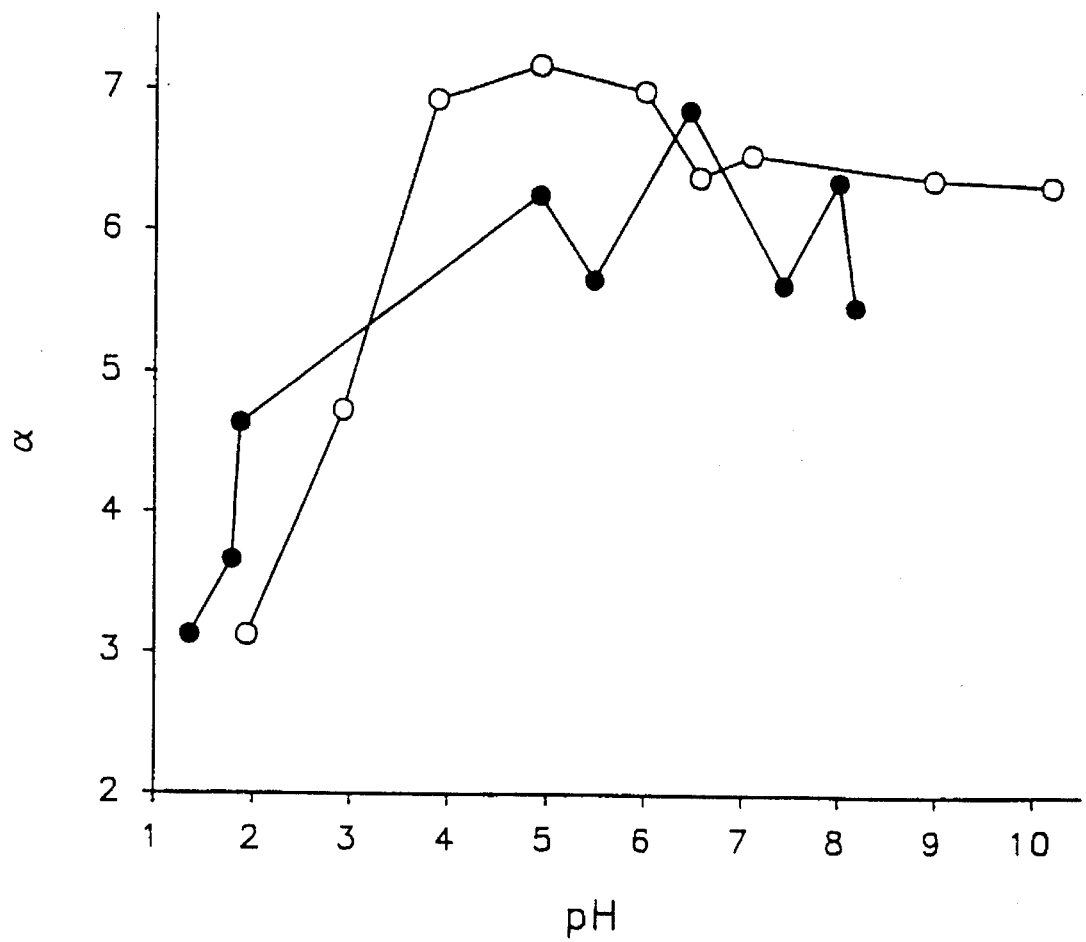
FIG. 10 is a graph of skin irritation ($\alpha$) as a function of cathodic reservoir pH.

Irritation and resistance values from TABLE 10 are plotted versus pH in FIGS. 6 and 7, respectively. Irritation and resistance values from TABLE 11 are plotted versus pH in FIGS. 8 and 9, respectively. Irritation values from TABLES 12 (open dot) and 13 (solid dot) are plotted versus pH in FIG. 10.

TABLE 10

| CATHODIC RESERVOIR COMPOSITION (all include 0.1M NaCl, 3% HPC, HCl q.s. to desired pH, and water q.s.) | CATHODIC RESERVOIR pH | SKIN RESISTANCE (R) (KOhms · cm$^2$) | SKIN IRRITATION (α) |
| --- | --- | --- | --- |
| 0.05M L-histidine base | 1.93 | 18.9 | 3.1 |
| 0.05M L-histidine base | 2.92 | 32.4 | 4.7 |
| 0.05M L-histidine base | 3.88 | 35.2 | 6.9 |
| 0.05M L-histidine base | 4.93 | 37.6 | 7.2 |
| 0.05M L-histidine base | 6.00 | 45.4 | 7.0 |

TABLE 10-continued

| CATHODIC RESERVOIR COMPOSITION (all include 0.1M NaCl, 3% HPC, HCl q.s. to desired pH, and water q.s.) | CATHODIC RESERVOIR pH | SKIN RESISTANCE (R) (KOhms · cm$^2$) | SKIN IRRITATION ($\alpha$) |
|---|---|---|---|
| 0.05M L-lysine base | 6.55 | 32.1 | 6.4 |
| 0.05M L-histidine base | 7.09 | 38.9 | 6.6 |
| 0.05M L-lysine base | 8.98 | 30.1 | 6.4 |
| 0.05M L-lysine base | 10.19 | 34.0 | 6.3 |

TABLE 11

| ANODIC RESERVOIR COMPOSITION (all include 0.1M NaCl, 3% HPC, NaOH q.s. to desired pH, and water q.s.) | ANODIC RESERVOIR pH | SKIN RESISTANCE (R) (KOhms · cm$^2$) | SKIN IRRITATION ($\alpha$) |
|---|---|---|---|
| 0.05M citric acid | 2.11 | 51.6 | 4.7 |
| 0.05M citric acid | 2.72 | 50.9 | 5.3 |
| 0.05M citric acid | 3.62 | 45.6 | 4.0 |
| 0.05M citric acid | 4.52 | 33.2 | 2.7 |
| 0.05M citric acid | 5.31 | 29.6 | 2.7 |
| 0.05M citric acid | 6.55 | 27.4 | 3.3 |
| 0.05M sodium phosphate monobasic | 7.47 | 23.4 | 2.6 |
| 0.05M boric acid | 8.80 | 22.5 | 2.5 |
| 0.05M boric acid | 9.93 | 23.5 | 2.5 |

TABLE 12

| CATHODIC RESERVOIR COMPOSITION (all include 0.1M NaCl, HPC, HCl q.s. to desired pH, and water q.s.) | CATHODIC RESERVOIR pH | SKIN IRRITATION ($\alpha$) |
|---|---|---|
| 0.05M L-histidine base | 1.93 | 3.1 |
| 0.05M L-histidine base | 2.92 | 4.7 |
| 0.05M L-histidine base | 3.88 | 6.9 |
| 0.05M L-histidine base | 4.93 | 7.1 |
| 0.05M L-histidine base | 6.00 | 7.0 |
| 0.05M L-lysine base | 6.55 | 6.4 |
| 0.05M L-histidine base | 7.09 | 6.6 |
| 0.05M L-lysine base | 8.98 | 6.4 |
| 0.05M L-arginine base | 10.19 | 6.4 |

TABLE 13

| CATHODIC RESERVOIR COMPOSITION (all include 0.1M NaCl, 3% HPC, NaOH q.s. to desired pH, and water q.s.) | CATHODIC RESERVOIR pH | SKIN IRRITATION ($\alpha$) |
|---|---|---|
| 0.15M phosphoric acid | 1.35 | 3.1 |
| 0.15M phosphoric acid | 1.78 | 3.7 |
| 0.15M phosphoric acid | 1.86 | 4.6 |
| 0.15M monobasic sodium phosphate | 4.92 | 6.3 |
| 0.15M monobasic sodium phosphate | 5.47 | 5.7 |
| 0.15M monobasic sodium phosphate | 6.45 | 6.9 |
| 0.15M monobasic sodium phosphate | 7.42 | 5.6 |
| 0.15M monobasic sodium phosphate | 8.00 | 6.4 |
| 0.15M monobasic sodium phosphate | 8.17 | 5.5 |

Because the buffer ions in this Example had a charge which was opposite the charge on the electrode (ie, positively charged buffer ions in the cathodic reservoir and negatively charged buffer ions in the anodic reservoir), a negligible amount of buffer ions were transported into the skin by electromigration. The skin irritation and skin resistance results were similar to those obtained in EXAMPLE I, ie, cathodic reservoir pH's of less than about 4 and/or anodic reservoir pH's of greater than about 4 result in reduced skin resistance and reduced skin irritation compared to cathodic reservoir pH's greater than about 4 and/or anodic reservoir pH's less than about 4. Furthermore, buffering of the reservoirs alone is sufficient to reduce skin irritation and skin resistance, and the charge of the buffer ion (which charge effects whether or not the buffer ion is delivered at a significant rate into the skin) does not appear to significantly affect the results, at least during short periods (ie, up to 30 minutes) of electrotransport administration.

EXAMPLE III

Cathodic reservoir compositions containing sodium phosphate buffers (negatively charged buffer ions) were evaluated in this set of experiments. All compositions contained 0.05M phosphoric acid, 0.1M sodium chloride, 6% polyvinyl alcohol, 4% hydroxypropyl methylcellulose, and q.s. water. Sodium hydroxide was added q.s. to achieve the desired pH.

In this set of experiments, the electrotransport was conducted on the inner arm of human volunteers. The skin contact area of the electrode reservoir gels (ie, both the anodic gel and the cathodic gel) were each approximately 5.1 cm$^2$, and the reservoir gel volume was about 800 μL. The anodic electrode was silver foil and the cathodic electrode was silver chloride (ie, silver foil treated with HCl to form a surface layer of AgCl). The electrodes were connected to a DC power source which delivered a constant current of 0.51 mA, resulting in a current density of about 0.1 mA/cm$^2$. Electrode gels were placed on the skin and connected to the DC power source. The power source delivered current through the gels for about 4 hours, after which time the electrodes were disconnected and the gels removed. After removal from the arms of the patients, the potassium content of the cathode gels was measured and potassium efflux (μg/cm$^2$.h) was calculated by dividing the measured potassium content by the product of gel skin contact area (ie, 5.1 cm$^2$) and time of application ( ie, 4 h).

Skin resistance was measured (as in Example I) at 1 hour after gel application and skin irritation measurements were taken about 24 hours after the gels were removed.

Figure 11:
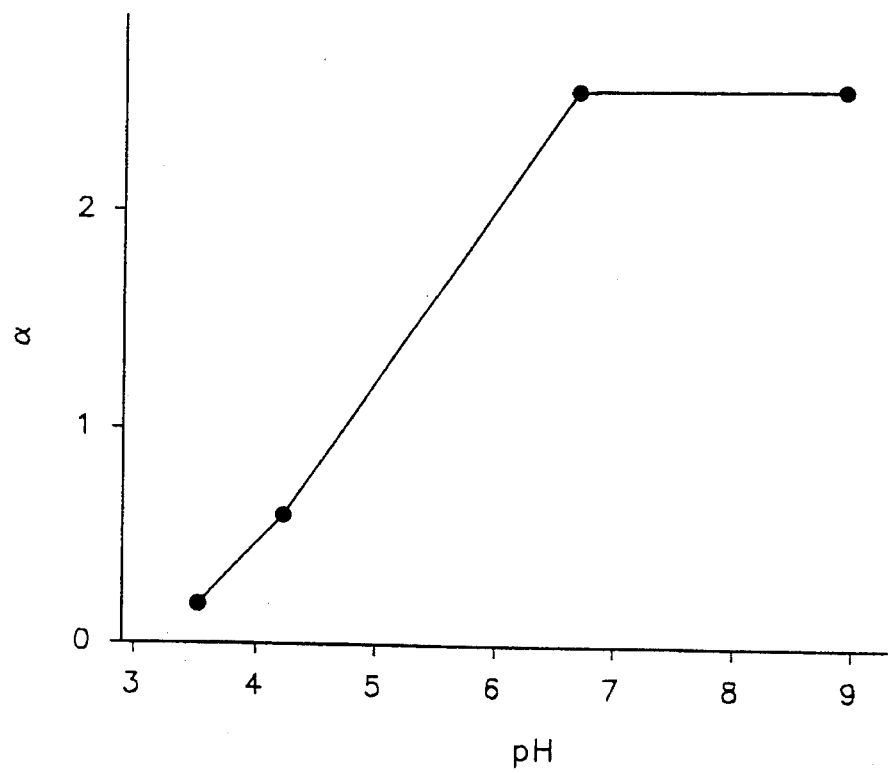
FIGS. 11 and 12 are graphs of skin irritation ($\alpha$) and skin resistance (R), respectively, as a function of cathodic reservoir pH.
Figure 12:
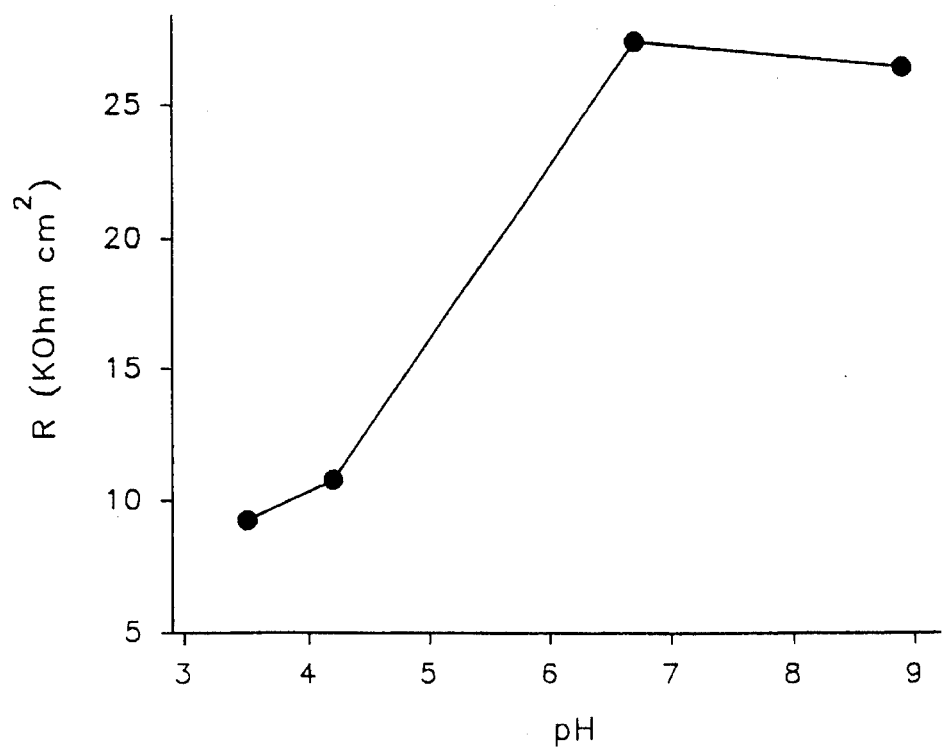

TABLE 14 gives averaged results for six subjects. FIGS. 11 and 12 illustrate plots of the skin irritation and skin resistance values, respectively, as a function of cathodic reservoir pH. Table 14 also lists the average potassium efflux values at each pH. The potassium efflux was about 2 μg/cm$^2$.h at pH values below about 4, when there was substantially no skin irritation or redness (ie, α of 0.2 or 0.6). Conversely, the potassium efflux was greater than 10 μg/cm$^2$.h at pH values of 6.7 and 8.9 when there was visible skin irritation and redness (ie, α of 2.6). While the mechanism responsible for the enhanced efflux of potassium accompanying skin irritation is unclear, the correlation between greater skin irritation/redness and higher potassium efflux is clearly demonstrated in Table 14. One possible explanation is that the applied electric current causes the skin cells to rupture or otherwise release their cytoplasmic potassium content. The cytoplasmic potassium concentration (ie, the potassium concentration within the skin cells) is about forty times greater than that of the interstitial fluid outside the skin cells. This at least suggests that skin irritation which occurred when electric current was applied at pH values greater than 4, caused expulsion of potassium from the interior of cells into the interstitial fluid, where it effluxed from the skin into the cathode hydrogel due to the applied electric field.

TABLE 14

| CATHODIC RESERVOIR pH | SKIN RESISTANCE (R) (KOhm · cm$^2$) | SKIN IRRITATION (α) | POTASSIUM EFFLUX (μg/cm$^2$ · h) |
| --- | --- | --- | --- |
| 3.5 | 9.1 | 0.2 | 2.1 |
| 4.2 | 10.6 | 0.6 | 2.0 |
| 6.7 | 26.9 | 2.6 | 13.4 |
| 8.9 | 26.0 | 2.6 | 18.6 |

In this EXAMPLE, negatively charged phosphate buffer ions were present in the cathodic reservoir and hence, were transported into the skin. As FIGS. 11 and 12 illustrate, the skin irritation and resistance results followed the same trend as in EXAMPLES I and II. At a cathodic reservoir pH of 3.5 to 4.2, the skin beneath the reservoir had resistances less than about 11 KOhm.cm$^2$ and irritation values of less than about 0.6. However, at the higher cathodic reservoir pH levels of 6.7 and 8.9, the skin resistances exceeded 25 KOhms.cm$^2$ and irritation values exceeded 2.5. Thus, cathodic reservoir pH below about 4 produced lower skin irritation and skin resistance than pH above about 4.

EXAMPLE IV

Cathodic reservoir formulations containing histidine chloride buffer (ie, positively charged histidine buffer ions) and sodium citrate buffer (ie, negatively charged citrate buffer ions) at pH 3 and 4 were studied. All compositions contained 0.1M buffer (histidine or citrate), 6% polyvinyl alcohol (PVA), 4% hydroxypropylmethylcellulose (HPMC), either HCl (for histidine) or NaOH (for citric acid) q.s. to the desired pH, and q.s. water.

As in EXAMPLE III, the electrotransport was conducted on the inner arm of human volunteers. The electrode materials, the gel volume and skin contact area, the current, the current density and the wearing time were the same as in Example III.

Skin resistance (R) was measured (as in Example I) at 0.5, 1, 2, 3 and 4 hours of wearing. Skin irritation (α) was measured (as in Example I) at 1, 4 and 24 hours after the end of wearing. Both R and α values are given in TABLE 15 as a function of buffer, pH, and number of hours after removal. Each data point for pH 4 represents an average of readings for seven human subjects, while for pH 3, each data point represents an average of eight human subjects.

TABLE 15 presents skin irritation ($\alpha$) as a function of hours after device removal for both citrate and histidine buffers at pH 3 and 4. Similarly, TABLE 16 presents skin resistance (R) as a function of hours after device removal for both citrate and histidine buffers at pH 3 and 4.

Figure 13:
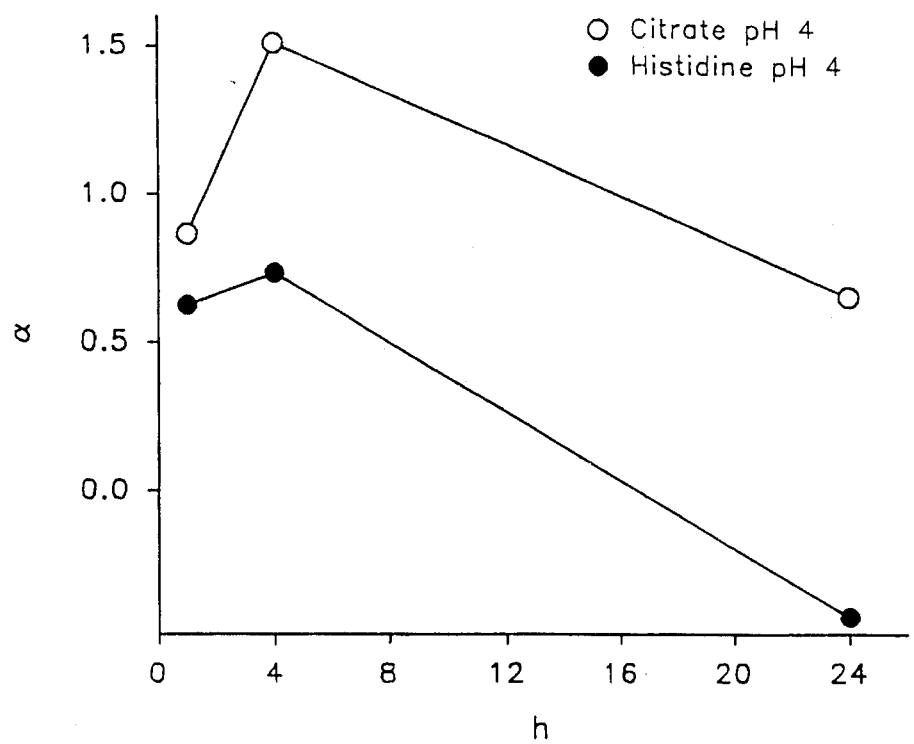
FIGS. 13 and 14 are graphs of skin irritation ($\alpha$) and skin resistance (R), respectively, as a function of hours after electrotransport device removal from the skin surface.
Figure 14:
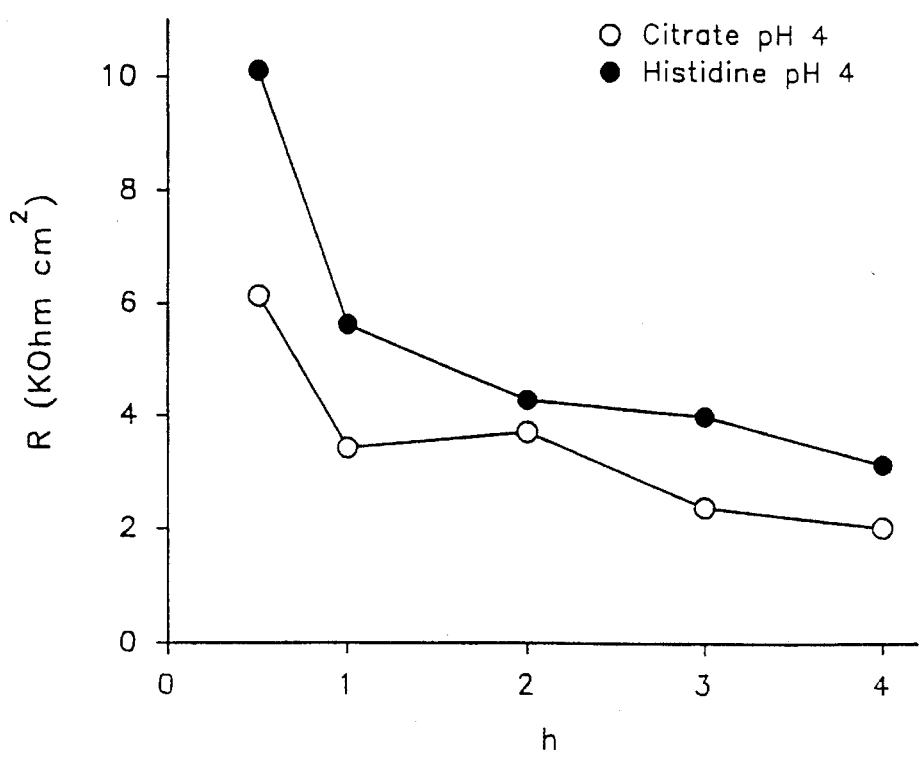
Figure 15:
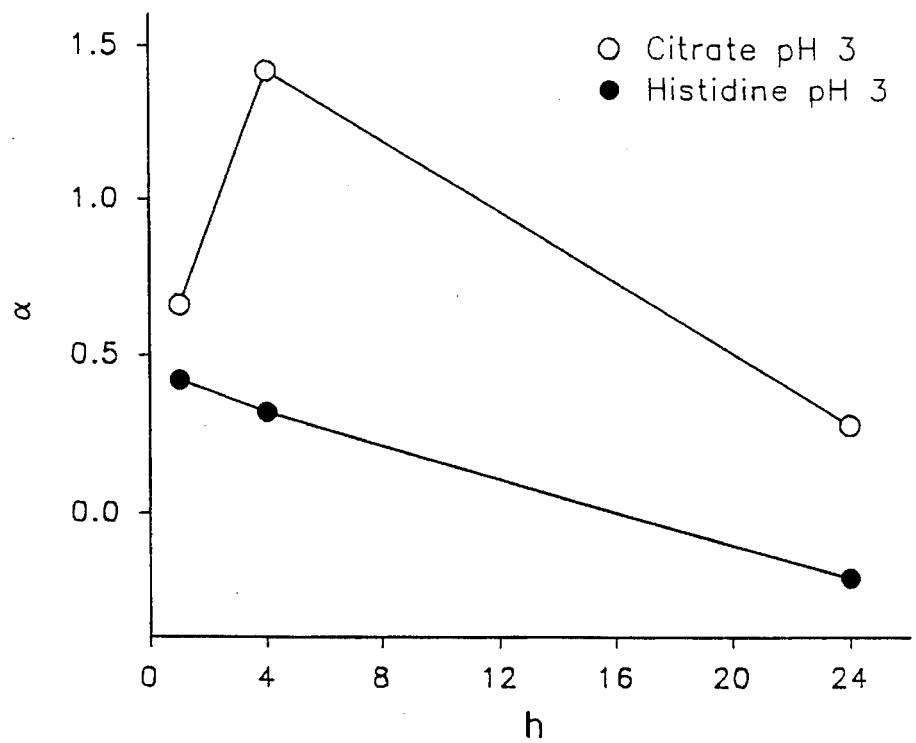
FIGS. 15 and 16 are graphs of skin irritation ($\alpha$) and skin resistance (R), respectively, as a function of hours after application of the electrotransport device to the skin surface.
Figure 16:
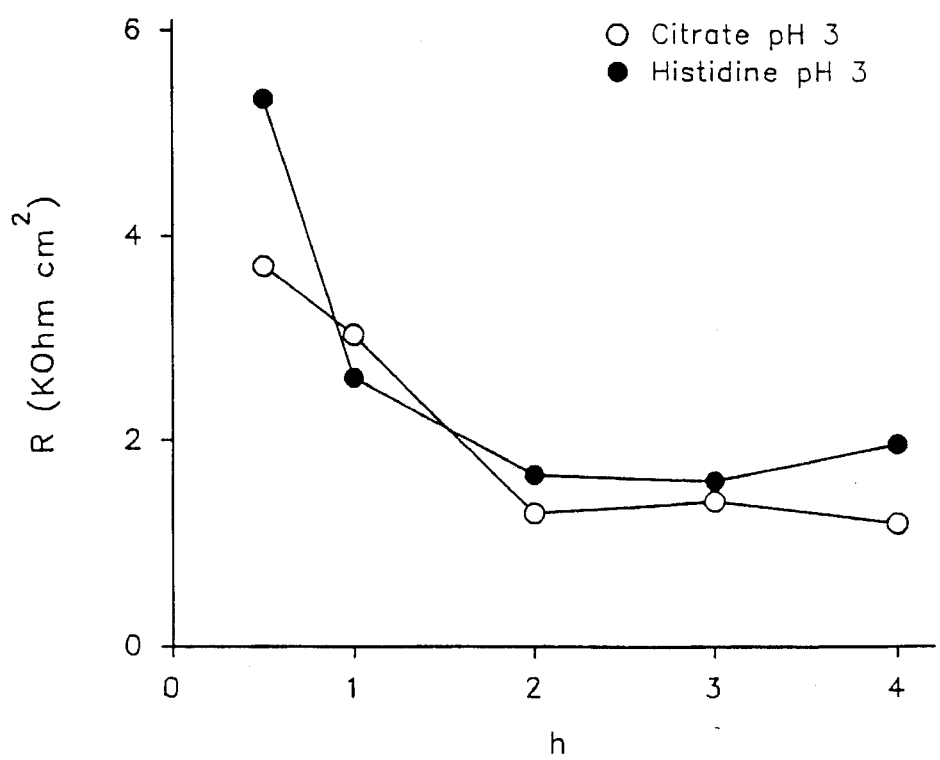

FIGS. 13 and 14 show plots of skin irritation ($\alpha$) and skin resistance (R), respectively, versus hours after device removal for citric acid and histidine buffers at pH 4. FIGS. 15 and 16 show plots of skin irritation ($\alpha$) and skin resistance (R), respectively, versus hours after device removal for citric acid and histidine buffers at pH 3.

TABLE 15

| Hours after device removal | Irritation ($\alpha$) at pH 3 for Histidine | Irritation ($\alpha$) at pH 3 for Citrate | Irritation ($\alpha$) at pH 4 for Histidine | Irritation ($\alpha$) at pH 4 for Citrate |
|---|---|---|---|---|
| 1 | 0.4 | 0.7 | 0.6 | 0.9 |
| 4 | 0.3 | 1.4 | 0.7 | 1.5 |
| 24 | −0.2 | 0.3 | −0.4 | 0.7 |

TABLE 16

| Hours after device removal | Resistance at pH 3 for Histidine (KOhm · cm$^2$) | Resistance at pH 3 for Citrate (KOhm · cm$^2$) | Resistance at pH 4 for Histidine (KOhm · cm$^2$) | Resistance at pH 4 for Citrate (KOhm · cm$^2$) |
|---|---|---|---|---|
| 0.5 | 5.3 | 3.7 | 10.1 | 6.1 |
| 1 | 2.6 | 2.0 | 5.6 | 3.4 |
| 2 | 1.7 | 1.3 | 4.3 | 3.7 |
| 3 | 1.6 | 1.4 | 4.0 | 2.4 |
| 4 | 2.0 | 1.2 | 3.1 | 2.0 |

In one set of tests, the cathodic reservoir contained positively charged histidine buffer, while in the other set, the is cathodic reservoir contained negatively charged citrate buffer. Hence, the citrate buffer ions were transported into the skin by electromigration while the histidine buffer ions were not. Although skin resistance values for the two buffers were not significantly different (See FIGS. 14 and 16), buffering the cathodic reservoir with histidine resulted in lower skin irritation compared to buffering with citric acid (See FIGS. 13 and 15). Therefore, preventing or at least minimizing buffer transport into the skin (ie, through use of a cationic buffer in the cathodic reservoir and/or an anionic buffer in the anodic reservoir) is preferred for minimizing skin irritation.

EXAMPLE V

Six electrolyte compositions were studied to determine the effect of cathodic reservoir pH on skin irritation. These compositions consisted of three ionic species (lactate, sulfate, and tartrate) in which two different pH's were evaluated for each ionic species. All reservoir electrolyte compositions were about 0.1 molar (M).

Current was applied at 100 $\mu$A/cm$^2$ for five hour periods. Skin resistance values were determined from Ohm's Law, by measuring the applied voltage after 5 hours and the current applied. After application of current was discontinued, the skin beneath the cathodic reservoir was visually evaluated for redness.

Irritation measurements are expressed on a relative scale in Table 17, as a function of pH and electrolyte composition. These ratings were determined by visually comparing, for erythema (redness), each treated skin site to every other treated skin site in the study. A rating of −1 for worse, 0 for substantially the same, and +1 for better was assigned to each comparison. The sums of these numbers represents a relative ranking of the sites for erythema, which sums are reported in Table 17. The visual determinations were made at one and 24 hours after current application was initiated. Three samples were evaluated for each electrolyte, ie n=3, and an averaged value is reported in TABLE 17. The reservoir composition which has the highest ranking produced the least irritation, and vice versa. The minimum possible value is zero, which would indicate that the three sites contacting that electrolyte were rated worse than all other sites. The maximum possible value is 34, which would indicate that the three sites in contact with that electrolyte were rated better than all other sites.

TABLE 17

| ELECTROLYTE | IONIC SPECIES | pH | AVERAGE IRRITATION RANKING AFTER 1 HOUR | AVERAGE IRRITATION RANKING AFTER 24 HRS | RESISTANCE (KOhm · cm$^2$) AFTER 5 HRS |
|---|---|---|---|---|---|
| sodium lactate | lactate | 5.5 | 8.3 | 2.0 | 18.3 |
| lactic acid | lactate | 2.2 | 12.0 | 11.0 | 10.1 |
| sodium sulfate | sulfate | 6.0 | 12.6 | 12.0 | 15.5 |
| sodium hydrogen sulfate | sulfate | 1.5 | 24.0 | 24.6 | 12.4 |

TABLE 17-continued

| ELECTROLYTE | IONIC SPECIES | pH | AVERAGE IRRITATION RANKING AFTER 1 HOUR | AVERAGE IRRITATION RANKING AFTER 24 HRS | RESISTANCE (KOhm · cm$^2$) AFTER 5 HRS |
|---|---|---|---|---|---|
| sodium tartrate | tartrate | 7.4 | 21.3 | 15.6 | 16.0 |
| sodium hydrogen tartrate | tartrate | 2.0 | 24.3 | 24.6 | 10.4 |

Table 17 shows that, for each ionic species studied, a lower pH produced lower comparative irritation rankings. Further, for each ionic species, a lower pH produced a lower skin resistance.

EXAMPLE VI

Cathodic reservoir formulations containing histidine chloride buffer adjusted to the desired pH with hydrochloric acid were placed on chest and arm sites of five different groups of human subjects. All sites were exposed to a DC current density of about 0.1 mA/cm$^2$ for 4 to 6 hours. After completion of each experiment, the potassium content of the cathode hydrogels was determined and potassium efflux values calculated.

Table 18 summarizes the potassium efflux values calculated for the five groups of subjects. This data confirms the strong correlation between pH and potassium efflux discussed in Example III. As in Example III, cathodic pH values greater than 4 correlated with a four to five-fold enhancement in potassium efflux.

TABLE 18

| Cathode Gel pH | Number of Subjects | Number of Sites Tested | Site Location | Potassium Efflux (μg/cm$^2$ · h) |
|---|---|---|---|---|
| 2.5 | 3 | 3 | Arm | 2.3 |
| 3 | 6 | 6 | Chest | 3.0 |
| 3 | 5 | 20 | Arm | 3.0 |
| 7 | 6 | 6 | Chest | 12.2 |
| 7 | 6 | 6 | Chest | 13.1 |

EXAMPLE VII

An electrotransport device for delivering lidocaine HCl and having a configuration as illustrated in FIG. 1, but without the membranes 30 and 32, is constructed. The anode 12 is comprised of silver and the cathode 14 is comprised of silver chloride. Both the anodic reservoir 16 and the cathodic reservoir 18 are comprised of a polyvinyl alcohol based hydrogel. Each of the reservoirs 16 and 18 has a volume of 1 cm$^3$ and a skin contact area of 10 cm$^2$. The reservoir 16 gel is imbibed with an aqueous solution of lidocaine HCl and the reservoir 18 gel is imbibed with an aqueous saline solution. A miniature potassium sensing probe sold by Microelectrodes, Inc. of Londenerry, N.H., Model No. MI-402 is inserted into the cathodic reservoir 18 and connected to the power source in circuit layer 24. The potassium sensing probe, and the control circuit therefor, are set to measure the potassium concentration in the cathodic reservoir every 0.1 h. The sensed concentration is compared to the previously sensed concentration by an electronic comparator. When the change in the potassium concentration exceeds 5 μg/cm$^3$ over the 0.1 h interval (ie, a rate of change of concentration of 50 μg/cm$^3$·h), which change in concentration corresponds to a potassium efflux of about 5 μg/cm$^2$·h, an LED which is visible from the exterior of the device is activated, thereby signalling the patient to move the device to another skin site.

Having thus generally described the invention and described in detail certain preferred embodiments thereof, it will be readily apparent that various modifications to the invention may be made by workers skilled in the art without departing from the scope of this invention, which is limited only by the following claims.

What is claimed is:

1. In a method of operating an electrotransport delivery device which delivers an agent by electrotransport under the influence of an electric current through a skin site, the device comprising an anodic electrode assembly, a cathodic electrode assembly, a source of electrical power electrically connected to the electrode assemblies and an agent reservoir in at least one of the electrode assemblies;

the improvement whereby electrotransport-induced irritation of the skin site can be reduced or avoided; which improvement comprises:
a) monitoring potassium concentration in the cathodic electrode assembly during electrotransport agent delivery; and
b) reducing the electric current flowing through the skin site when the potassium concentration reaches a value which corresponds to a predetermined potassium efflux level associated with electrotransport-induced irritation of the skin.

2. The method of claim 1 wherein the electric current is reduced to substantially zero.

3. The method of claim 1 wherein the reduction in electrical current flowing through the skin site is produced in response to a patient-detectable signal generated by the device.

4. The method of claim 3 wherein the reduction in electrical current is obtained by removing said delivery device from the skin site in response to the signal.

5. The method of claim 4, including thereafter delivering the agent by electrotransport through said another skin site.

6. The method of claim 4 further comprising the step of reapplying the device to another skin site.

7. The method of claim 1 wherein said potassium efflux level is no greater than 10 μg/cm$^2$/hr.

8. An electrotransport device for delivering an agent through a skin site under the influence of an electrical current, said device being capable of reducing irritation associated with such delivery, said device comprising:
a) an anodic electrode assembly and a cathodic electrode assembly;
b) an agent reservoir in at least one of said electrode assemblies;

c) a source of electrical power electrically connected between said electrode assemblies whereby an electrical current can be caused to flow between said electrode assemblies through said agent reservoir and said skin site;

d) means for monitoring the concentration of potassium in said cathodic electrode assembly during electrotransport administration of said agent; and e) means for emitting a signal alerting the patient when said monitoring means detects an increase in the potassium concentration to a value which corresponds to a predetermined potassium efflux level associated with electrotransport-induced irritation of the skin.

9. The device of claim 8 further comprising a controller for reducing the electric current applied by the device in response to said signal.

10. An electrotransport device for delivering an agent through a skin site under the influence of an electrical current, said device being capable of reducing irritation associated with such delivery, said device comprising:

a) an anodic electrode assembly and a cathodic electrode assembly;

b) an agent reservoir in at least one of said electrode assemblies;

c) a source of electrical power electrically connected between said electrode assemblies whereby an electrical current can be caused to flow between said electrode assemblies through said agent reservoir and said skin site;

d) means for monitoring the concentration of potassium in said cathodic electrode assembly during electrotransport administration of said agent; and e) means for emitting a signal to a controller when said monitoring means detects an increase in the potassium concentration to a value which corresponds to a predetermined potassium efflux level associated with electrotransport-induced irritation of the skin;

f) a controller for reducing the electric current applied by the device in response to receiving said signal.

11. The device of claim 9 or 10 wherein the controller reduces the applied electric current to substantially zero.

12. The device of claim 10 or 8 wherein said signal is emitted when the potassium concentration reaches a predetermined value.

13. The device of claim 10 or 8 wherein said signal is emitted when the rate of change of potassium concentration reaches a predetermined value.

14. The device of claim 10 or 8 wherein the potassium sensor comprises a potassium sensing electrode.

15. The device of claim 10 or 8 wherein said potassium efflux level is no greater than 10 µg/cm$^2$/hr.

* * * * *